（12）United States Patent
Carrison

(10) Patent No.: US 11,857,195 B2
(45) Date of Patent: Jan. 2, 2024

(54) VESSEL FLOW CONTROL DEVICES AND METHODS

(71) Applicant: Harold Carrison, Pleasanton, CA (US)

(72) Inventor: Harold Carrison, Pleasanton, CA (US)

( * ) Notice: Subject to any disclaimer, the term of this patent is extended or adjusted under 35 U.S.C. 154(b) by 433 days.

(21) Appl. No.: 17/033,302

(22) Filed: Sep. 25, 2020

(65) Prior Publication Data

US 2021/0007747 A1    Jan. 14, 2021

Related U.S. Application Data

(60) Division of application No. 15/389,253, filed on Dec. 22, 2016, now abandoned, which is a continuation of application No. 13/958,313, filed on Aug. 2, 2013, now Pat. No. 9,561,035.

(60) Provisional application No. 61/679,613, filed on Aug. 3, 2012.

(51) Int. Cl.
| | |
|---|---|
| *A61B 17/12* | (2006.01) |
| *A61F 2/90* | (2013.01) |
| *A61F 2/86* | (2013.01) |
| *A61B 17/00* | (2006.01) |
| *A61F 2/06* | (2013.01) |
| *A61B 90/00* | (2016.01) |

(52) U.S. Cl.
CPC .... *A61B 17/1204* (2013.01); *A61B 17/12027* (2013.01); *A61B 17/12031* (2013.01); *A61B 17/12036* (2013.01); *A61B 17/12045* (2013.01); *A61B 17/12109* (2013.01); *A61B 17/12136* (2013.01); *A61B 17/12177* (2013.01); *A61F 2/86* (2013.01); *A61F 2/90* (2013.01); *A61B 2017/00004* (2013.01); *A61B 2090/064* (2016.02); *A61F 2002/068* (2013.01); *A61F 2250/0031* (2013.01)

(58) Field of Classification Search
CPC .......... A61M 2025/1052; A61M 25/10; A61M 25/1018; A61F 2002/068; A61B 17/1204; A61B 17/12027; A61B 17/12031; A61B 17/12036; A61B 17/12109; A61B 17/12136; A61B 17/12177
See application file for complete search history.

(56) References Cited

U.S. PATENT DOCUMENTS

| | | | | |
|---|---|---|---|---|
| 5,084,060 | A * | 1/1992 | Freund | A61M 25/10184 |
| | | | | 604/920 |
| 2004/0064091 | A1 * | 4/2004 | Keren | A61B 17/12036 |
| | | | | 600/16 |

* cited by examiner

*Primary Examiner* — Katherine M Shi

(74) *Attorney, Agent, or Firm* — Polsinelli PC

(57) ABSTRACT

Systems and methods for treating an afflicted vessel and/or vessel associated with an afflicted tissue of a mammalian patient are presented herein. In particular, devices for the control of flow rate and/or pressure within a vessel of a mammalian patient, and methods of treating an afflicted vessel and/or a vessel associated with an afflicted tissue using the devices are presented herein.

18 Claims, 13 Drawing Sheets

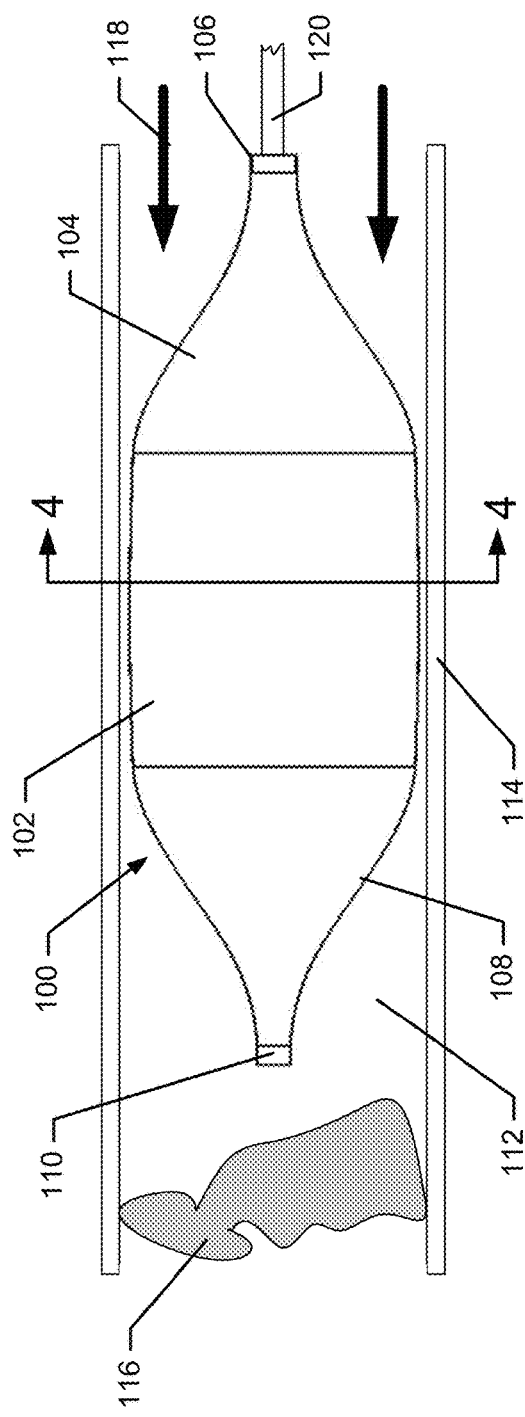
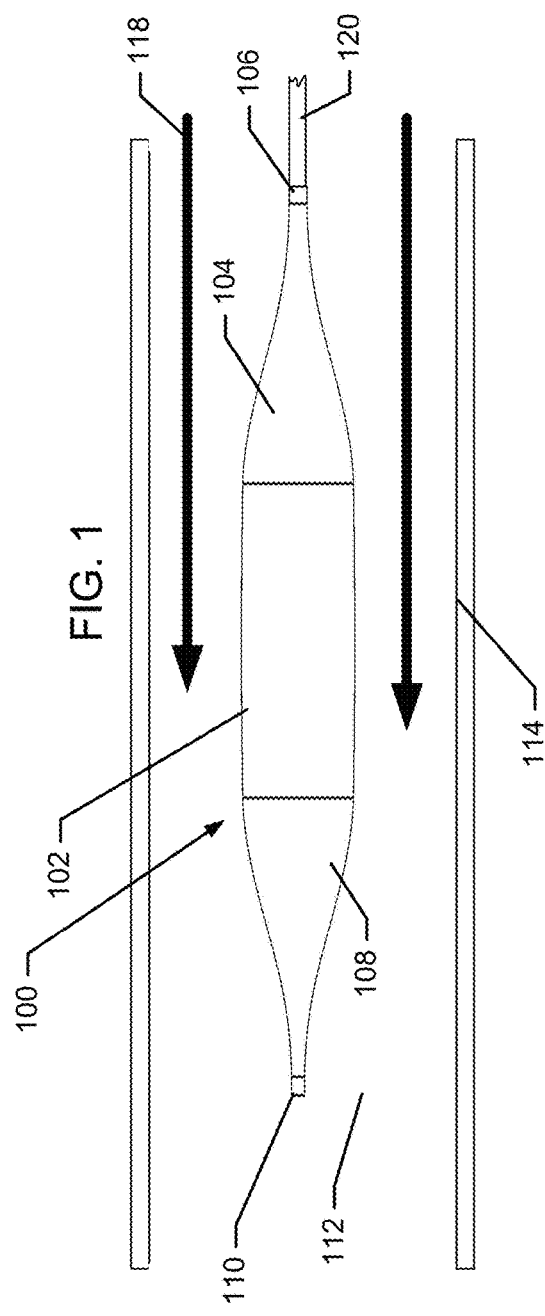

VESSEL FLOW CONTROL DEVICES AND METHODS

CROSS-REFERENCE TO RELATED APPLICATIONS

The present application is a divisional of U.S. application Ser. No. 15/389,253 filed Dec. 22, 2016, which application is a continuation of U.S. application Ser. No. 13/958,313 filed Aug. 2, 2013, now U.S. Pat. No. 9,561,035, which application claims priority to U.S. Provisional Patent Application No. 61/679,613, which was filed on Aug. 3, 2012, and is entitled Vessel Flow Control Devices and Methods. The contents of the above-mentioned patent applications are hereby incorporated by reference in their entirety.

FIELD OF THE INVENTION

Aspects of the present invention relate to systems and methods related to the treatment of an afflicted vessel and/or vessel associated with an afflicted tissue of a mammalian patient. More specifically, the present invention relates to devices for the control of flow rate and/or pressure within a vessel of a mammalian patient, and methods of treating an afflicted vessel and/or a vessel associated with an afflicted tissue using the devices.

BACKGROUND OF THE INVENTION

A variety of afflictions such as peripheral vascular disease, ischemic strokes, and various other infarctions such as myocardial infarctions, pulmonary infarctions, splenic infarctions, limb infarctions, and avascular necrosis of bone tissue, are associated with blockages of blood vessels in a human patient, usually due to thrombi (blood clots) or excessive plaque buildup. Because the tissues associated with a blood vessel typically rely upon that vessel for a continuous supply of oxygen and nutrients, a blockage of that vessel create stresses on these associated tissues, as well as the vascular tissues themselves. As a result, effective treatment of an affliction associated with a blockage of a blood vessel may be complicated by the response of the weakened vascular tissues to the restored blood flow, and the associated elevation of flow velocity and blood pressure. The treatment of ischemic strokes presents a particularly poignant example of the interplay of the condition of the vascular tissues and the outcome of a treatment.

Ischemic strokes, defined herein as the rapid loss of a brain function due to a sudden disruption of the brain's blood supply due to a blood clot, are a leading cause of death worldwide. Those fortunate enough to survive an ischemic stroke may still face significant losses of brain function such as loss of the ability to move one or more limbs on one side of the body, loss of the ability to understand or formulate speech, and/or an inability to see one side of the visual field. Current treatments for ischemic strokes must be completed within 3 to 6 hours of the stroke due to the associated weakening of the brain vascular tissues. Strokes associated with the disruption of flow within relatively large circulatory vessels must be treated quickly due to the larger area of the brain infracted, the resultant lower coverage of blood flow to the surrounding tissue from collateral vessels, as well as the potentially devastating and significant loss of function.

If the stroke is not treated within this relatively brief window of opportunity, removal of the clot to restore blood flow carries with it a significant risk of a secondary hemorrhagic event resulting in additional brain damage or death of the patient. As a result, a high proportion of physicians are relatively reluctant to remove blood clots outside of this treatment window, and patients are instead forced to cope with the functional deficits associated with the loss of brain function associated with the stroke event. Unfortunately, current treatment methods are unable to control the rate at which blood pressure and flow rate are restored to ischemic brain tissues and associated weakened blood vessels.

The use of current treatment methods are further limited by the inherent difficulty in pin-pointing the time at which a stroke occurred, as well as the challenge of transporting a patient to a facility capable of implementing one of these current treatment methods. For example, patients presenting with a stroke upon awakening from sleep are not strong candidates for current treatment methods due to the inability to identify the time of onset of the stroke. The time elapsed during a stroke event, the time taken to recognize that a stroke is occurring, the time taken to signal a need for assistance, the time taken for medical personnel to reach the patient, the time taken to transfer the patient to a treatment facility, and the time taken to diagnose the stroke condition all narrow the already-brief window of opportunity for treatment using existing methods. As a result, a significant number of patients are not viable candidates for treatment using existing methods.

There exists a need in the art for a device capable of controlling the flow rate and/or pressure within an afflicted vessel and/or a vessel associated with an afflicted tissue. A need in the art further exists for a method of treating an afflicted vessel and/or a vessel associated with an afflicted tissue using the device to vary the flow rate and/or pressure within the vessel as a treatment and/or in conjunction with an additional treatment.

BRIEF SUMMARY OF THE INVENTION

In one aspect, a vessel flow control device for controlling a flow rate and/or a pressure within a vessel of a mammalian patient during a treatment is provided. The device includes a variable occlusion element that assumes a plurality of occlusion states. Each occlusion state has an occlusion factor ranging from about 5% to about 100%, and the occlusion factor is defined as the percentage of the lumen cross-sectional area occluded by a cross-sectional area of the variable occlusion element. For example, the occlusion factor of 100% corresponds to a complete blockage of flow through the vessel. The device is situated within a lumen of the vessel.

In another aspect, a vessel flow control device for controlling a flow rate and/or a pressure within a vessel of a mammalian patient during a treatment is provided. The vessel flow control device includes at least one balloon situated within a lumen of the vessel. The balloon includes a cylindrical body, a tapered proximal end projecting proximally from the body and ending in a proximal opening, and a tapered distal end projecting distally from the body opposite to the proximal end and ending in a distal opening. The balloon also includes an inner membrane formed into a closed cylindrical shape enclosing a cylindrical lumen; the lumen extends from the proximal opening to the distal opening of the balloon. In addition, the balloon includes an outer membrane sealed to the inner membrane at the proximal end and at the distal end. Together, the outer membrane and inner membrane enclose an essentially toroidal volume. In this aspect, the balloon is inflated and/or deflated to assume a plurality of occlusion states with an occlusion factor ranging from about 5% to about 100%.

In an additional aspect, a vessel flow control device for controlling a flow rate and/or a pressure within a vessel of a mammalian patient during a treatment is provided. The vessel flow control device includes a proximal balloon and a distal balloon. The balloons are situated within a lumen of the vessel at a separation distance ranging from about 1 inch to about 3 inches. The proximal balloon and the distal balloon each include a cylindrical body, a tapered proximal end projecting proximally from the body and ending in a proximal opening, and a tapered distal end projecting distally from the body opposite to the proximal end and ending in a distal opening. The proximal balloon and the distal balloon each further include an inner membrane formed into a closed cylindrical shape enclosing a cylindrical lumen extending from the proximal opening to the distal opening. The proximal balloon and the distal balloon also further include an outer membrane sealed to the inner membrane at the proximal end and at the distal end; the outer membrane and inner membrane enclose an essentially toroidal volume. The proximal balloon and the distal balloon each is inflated and/or deflated to assume a plurality of occlusion states with an occlusion factor ranging from about 5% to about 100%.

In another additional aspect, a method of treating an afflicted region of a vessel of a mammalian patient is provided. The method includes situating a vessel flow control device within a lumen of the vessel upstream of the afflicted region. The device includes a variable occlusion element that assumes a plurality of occlusion states; each occlusion state has an occlusion factor ranging from about 5% to about 100%. The method further includes configuring the device to assume an initial occlusion state with an occlusion factor of 100%, and gradually configuring the device to assume at least one intermediate occlusion state and a final occlusion state. Each successive intermediate occlusion state has a lower occlusion factor than the previous intermediate occlusion state, and the final occlusion state has an occlusion factor of about 5%. The device is gradually configured from the initial occlusion state to the final occlusion over a predetermined treatment period.

In yet another addition aspect, a vessel flow control device for controlling a flow rate and/or a pressure within a vessel of a mammalian patient during a treatment is provided. The vessel flow control device includes a stent device that includes a coated expandable cylindrical element enclosing a biodegradable material that forms a channel through which a vessel flow may pass when the material is biodegraded.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The following figures illustrate various aspects of the invention.

FIG. 1 is a longitudinal cross-sectional view of a balloon device in an inflated position.

FIG. 2 is a longitudinal cross-sectional view of a balloon device in a deflated position.

FIG. 4A is an illustration of the four lobes of the toroidal volume when the balloon device is inflated. FIG. 4B is an illustration of the four lobes of the toroidal volume when the balloon device is deflated.

FIG. 5A is an illustration of the inflated balloon device including a toroidal volume bounded by an outer membrane and an inner membrane. FIG. 5B is an illustration of an expanded inner membrane and dilated inner lumen.

FIG. 6A illustrates an intact outer coating. FIG. 6B illustrates the outer coating in a biodegraded condition. FIG. 6A illustrates the intact inner coating. FIG. 6B illustrates the inner coating in a biodegraded condition.

Corresponding reference characters and labels indicate corresponding elements among the views of the drawings. The headings used in the figures should not be interpreted to limit the scope of the claims.

DETAILED DESCRIPTION

Figure 3:
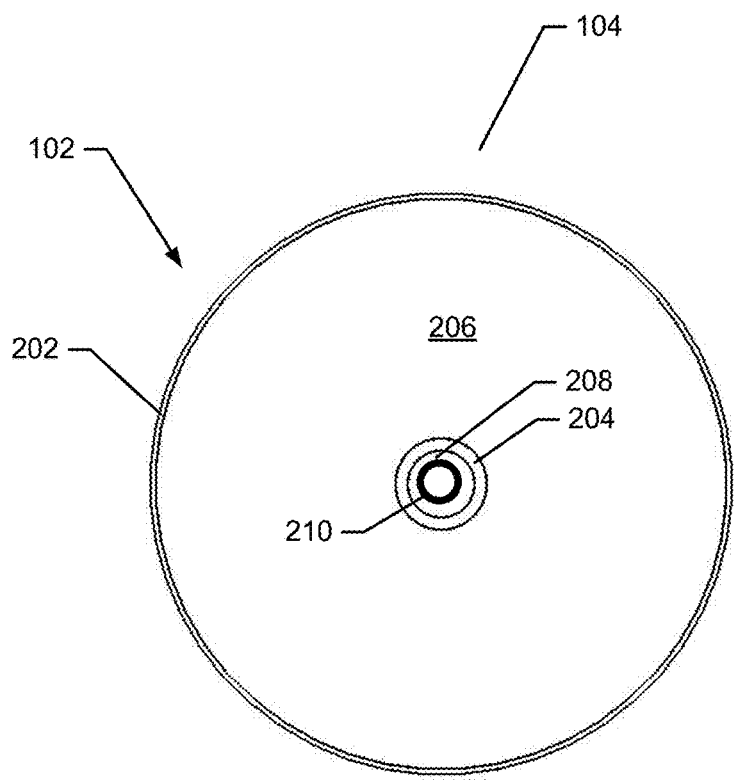
FIG. 3 is a transverse cross-sectional view through the balloon body as taken through section line 4-4 in FIG. 1.

Provided herein are devices for controlling the flow rate and/or pressure within a vessel of a mammalian patient. In general, the devices in various aspects may occlude the vessel in a controlled manner to implement a treatment of an afflicted region. For example, in the case of vascular tissue injury associated with an ischemic stroke, the device in one aspect may be used to completely occlude the blood flow entering an area of clot-related vascular damage, also referred to herein as the penumbra. The device may also be used to gradually restore blood pressure and blood flow to the region as the injured vascular tissue is healed. In other aspects, the device may further deliver one or more substances to the vascular tissue occluded by the device to aid in the recovery of the vascular tissue during the treatment. In additional aspects, the devices may further include instrumentation to assess blood flow and/or blood pressure in the afflicted region of the patient to provide information regarding the health and/or functional status of the vascular tissue, the degree of occlusion imparted by the device to the vessel, and any other relevant information regarding the condition or flow environment of the afflicted region of the patient.

Also provided herein are methods of using the devices for controlling the flow rate and/or pressure within a vessel of a mammalian patient. In one embodiment, the device may be operatively contacted with a vessel associated with an afflicted region such that the vessel is completely occluded initially. The configuration of the device may be gradually altered over time to reduce the device-related occlusion within the vessel. The configuration of the device may be altered according to a fixed and predetermined scheduled in one aspect, or the configuration may be altered based on assessments of the health and function of the vessel and/or afflicted tissue, either manually or by means of a feedback-based control system in other aspects.

For example, the device may be operatively contacted with a blood vessel associated with an ischemic stroke such that the vessel is completely occluded. According to a predetermined or feedback-based schedule, the configuration of the device may be gradually altered to reduce the occlusion and thereby increase the flow rate and pressure within the vessel. Based on subsequent measurements of the health and function of the vessel and/or afflicted tissue, the configuration of the device may be adjusted to increase the occlusion if the measurements indicate degradation of the tissue or vessel and to decrease the occlusion if the measurements indicate the enhanced health and function of the afflicted tissues and associated vessel. In additional aspects, therapeutic compounds may be introduced into the afflicted area by the device to enhance the health and function of the afflicted tissues and associated vessel at any time during the treatment, including during full occlusion of the vessel by the device. The other additional aspects, the device may further include other means of treating the afflicted tissues. For example, in the case of treatment of an ischemic stroke using an aspect of the devices described herein, the device may further include additional features that allow the clot associated with the ischemic event to be removed from the afflicted vessel prior to subsequent treatment as described herein.

In an aspect, the mammalian patient may be any mammalian organism. Non-limiting examples of mammalian organisms that are suitable patients in various aspects of the method include mammals from the Order Rodentia (mice); the Order Logomorpha (rabbits); the Order Carnivora, including Felines (cats) and Canines (dogs); the Order Artiodactyla, including Bovines (cows) and Suines (pigs); the Order Perissodactyla, including Equines (horses); and the Order Primates (monkeys, apes, and humans). In another aspect, the patient is a human.

Any size, type, and/or location of vessel within the mammalian patient may be treated using the devices and methods described herein without limitation, so long as the device is capable of operatively contacting the vessel in order to control the flow rate and/or pressure as described herein. In various aspects, the vessel may include any biological structure, tissue, or organ capable of convectively transporting a fluid at a flow rate. Non-limiting examples of vessels include circulatory vessels, urinary tract vessels, digestive tract vessels, respiratory vessels, and ventricular system vessels. Non-limiting examples of circulatory vessels include capillaries, arterioles, venules, arteries, veins, hearts, lymph nodes, and lymphatic vessels. Non-limiting examples of urinary tract vessels include kidneys, ureters, bladders, and urethras. Non-limiting examples of respiratory vessels include oropharynxes, nasopharynxes, larynxes, tracheas, bronchi, bronchioles, and alveoli.

The diameters of the circulatory vessels may range between about 10 µm and about 2 cm. In an aspect, if the device operatively contacts the vessel by implantation within the vessel, the vessels suitable for treatment by the device may be limited to those vessels large enough to accommodate the device and associated equipment including, but not limited to, a delivery device.

The devices and methods of various aspects may be used as a treatment, or as part of a treatment, for a variety of afflictions. Non-limiting examples of afflictions amenable to treatment using aspects of the device and method include: ischemic strokes and other clot-related infarctions such as myocardial infarctions, pulmonary infarctions, splenic infarctions, limb infarctions, and avascular necrosis of bone tissue, various forms of cancers/tumors, aneurysms, stenosis dissolution, and diabetes-related circulatory afflictions.

Various aspects of the vessel flow control devices and methods of using the devices to treat an affliction in a mammalian patient are present herein below.

I. Vessel Flow Control Device

In various aspects, the vessel flow control device may provide features to control the rate of flow and/or the pressure within a vessel in a selected region within a mammalian patient. Typically, this selected region may be an afflicted region associated with a vessel and/or an afflicted vessel. Non-limiting examples of vessels within selected regions include a vessel blocked by a clot or other structure within an infracted region; or a vessel providing blood to a region of tumor tissue. In an aspect, the vessel flow control device provides a number of useful functions when placed in operative connection with a vessel of a patient, including, but not limited to: complete obstruction of flow through the vessel; restoration of unobstructed flow through the vessel according to a predetermined schedule or in response to measurements related to the assessment of the health and/or function of the vessel; controlled release of one or more compounds to provide oxygen, nutrients, and or treatment to the vessel and/or associated region of the patient.

a. External Vessel Flow Control Devices

The vessel flow control device may be an external vessel flow control device operatively connected to the outside of the vessel of the patient in one aspect. In this aspect, the external vessel flow control device may include clamps and any other known suitable mechanical flow restriction element to releasably restrict flow through the vessel of the patient by a physical method. In another aspect, the vessel flow control device may include one or more electrodes applied externally to the vessel of the patient; activation of the electrodes may stimulate the contraction of smooth muscle tissue surrounding the vessel, resulting in the restriction of flow through the vessel. In yet another aspect, chemical vessel restrictors including, but not limited to dopamine and LEVOPHED, as well as chemical vessel dilators including, but not limited to, papaverine, may be administered in a sequence and amount sufficient to induce the constriction and dilation of the vessel according to a predetermined schedule.

b. Implanted Vessel Flow Control Devices

In another aspect, the vessel flow control device may be operatively connected by implanting the device within the lumen of the vessel upstream of the afflicted region. In this aspect, the device may be capable of reversibly or irreversibly changing shape, resulting in a change in cross-sectional area. At one extreme, the device may assume a shape having a cross-sectional area that completely blocks the lumen cross-sectional area, corresponding to an occlusion factor of 100%. The device may also assume a shape having a cross-sectional area that partially blocks the lumen cross-sectional area, corresponding to an occlusion factor of less than 100%. At another extreme, the device may assume a shape having a cross-sectional area that has essentially no blocking effect on the lumen cross-sectional area, corresponding to an occlusion factor of 0%. Occlusion factor, as used herein, describes the ratio of the cross-sectional area of vessel flow control device divided by the cross-sectional area of the vessel lumen expressed as a percentage.

The implanted vessel flow control devices may be implanted within a vessel using a delivery device. Any known delivery device may be used to situate and secure the implanted vessel flow control devices in place including, but not limited to, catheters and guide wires. In aspect, the delivery device may be selected in order to fit within the vessel to be treated using the device. Non-limiting examples of catheters suitable for situating the implanted vessel flow control devices within the vessel include: neurovascular catheters; peripheral venous catheter (PVC); central venous catheters; arterial catheters; non-tunneled catheters including Quinton catheters; tunneled catheters including Hickman catheters, Broviac catheters, Groshong catheters, and peripherally inserted central catheters (PICC or PIC lines); balloon catheters; balloon-tipped catheters; coaxial Teflon catheters; irrigation catheters; intracardiac catheters; bronchospirometry catheters; and pulmonary artery catheters including Swan-Ganz catheters.

The delivery device may be operatively attached to the implanted vessel flow control device. In addition, the delivery device may include elements to enhance the function of the implanted vessel flow control device including, but not limited to: tools for expanding or deploying a stent-type device; fluid supplies for inflating balloon-type devices; light sources and/or cameras for visualizing the implantation area; and conduits for the delivery of active compounds to treat the vessel. The conduits may also deliver other compounds including, but not limited to biodegrading agents to initiate the biodegrading of structural elements and/or coatings of the implanted vessel flow control devices.

In an aspect, the implanted vessel flow control device may remain attached to the delivery device throughout a treatment of a vessel, and may further be used to remove at least part of the implanted vessel flow control device upon completion of the treatment. In another aspect, the delivery device may be detached from the implanted vessel flow control device before, during, or after the treatment. In this aspect, the implanted vessel flow control device may remain implanted within the patient after completion of the treatment, or at least a portion of the implanted vessel flow control device may be removed from the patient after the treatment using a recovery device. Any known recovery device known in the art may be used without limitation including, but not limited to, a recovery wire and/or a recovery catheter.

If the implanted vessel flow control device remains implanted within the patient after the completion of the treatment, the implanted vessel flow control device may incorporate additional features to enhance the post-treatment function of the implanted vessel flow control device. For example, the implanted vessel flow control device may include an active compound such as a clot-inhibiting compound in any known time-released form including, but not limited to, a time-release coating that includes the active compound. In another example, at least a portion of the implanted vessel flow control device, up to and including the entire implanted vessel flow control device, may be constructed from a biodegradable material that is resorbed following the treatment.

A biodegradable material, as used herein, refers to any material that biodegrades after exposure to the physical, biological, and/or chemical environment within the vessel. The biodegradable material may biodegrade spontaneously, or the biodegradable material may biodegrade after exposure to an extrinsic biodegrading agent introduced into the vessel. In an aspect, the biodegradation may occur by means of a mechanism that avoids releasing particles of biodegradable material into the vessel that may cause secondary blockages within the vessel. Non-limiting examples of suitable mechanisms by which the biodegradation may occur include: dissolving, leeching, resorption, and any combination thereof.

The implanted vessel flow control devices may be provided in a variety of forms without limitation. Non-limiting examples of implanted vessel flow control devices include: balloon devices including at least one implanted inflatable/deflatable balloon, stent devices including a stent capable of expanding/contracting or biodegrading according to a predetermined schedule; and other biodegradable implants capable of biodegrading according to a predetermined schedule or in response to exposure to a dissolving agent. The implanted vessel flow control devices including balloon devices, stent devices, and other biodegradable implants are described herein below.

i. Balloon Devices

The implanted vessel flow control device may be a balloon device in one aspect. FIG. 1 is a longitudinal cross-sectional view of a balloon device 100 in one aspect. The balloon device 100 may include a balloon body 102 that has a roughly cylindrical shape when inflated. The balloon device 100 may further include a tapered proximal end 104 projecting in a proximal direction from the balloon body 102; the proximal end 104 further contains a proximal opening 106. The balloon device 100 may further include a tapered distal end 108 containing a distal opening 110 projecting in a distal direction from the balloon body 102 opposite to the proximal end 104.

The balloon 100 may be situated within a lumen 112 of a vessel 114 upstream relative to a clot 116 or other obstructive structure using a delivery device 120. The term "upstream", as used herein, may be defined by the direction of the flow 118 within the lumen 112 of the vessel. When fully inflated, the balloon body 102 may expand to a diameter essentially equal to the diameter of the vessel lumen when fully inflated, as illustrated in FIG. 1. In this configuration, the balloon device 100 has an occlusion factor of 100%, and no flow may pass the balloon body 102.

When the balloon device has an occlusion factor of 100%, the region of the blood vessel 114 situated downstream of the balloon device 100 experiences essentially zero flow speed and relatively low pressure. Without being limited to any particular theory, the low pressure and zero flow speed in this downstream region may provide conditions well-suited for the recovery and healing of any vascular tissue within the downstream region that may be weakened by the formation and/or removal of the clot 116.

If the clot 116 is removed from the lumen 112, the flow 118 through the vessel 114 may be reestablished up to physiological flow speeds and flow pressures. In an aspect, the balloon device 100 may be deflated as illustrated in FIG. 2 as a longitudinal cross-sectional view, causing a reduction in the diameter of the balloon body 102 such that the cross-sectional area of the balloon body 102 no longer fills the cross-sectional area of the lumen 112, resulting in an occlusion factor of less than 100%. In this configuration, the flow 118 within the vessel 114 may pass the balloon body 102 in the annular space formed between the balloon body 102 and the lumen 112; this reestablishment of flow in the vessel 114 results in a rise in the flow rate and pressure downstream of the balloon device 100. In an aspect, the balloon may be deflated over a period of time sufficient to allow for the healing of the vascular tissues injured by the clot 116. The rate at which the balloon device 100 may be deflated to reestablish flow within the vessel may be specified using a variety of methods discussed in detail herein below. In another aspect, the deflated balloon may be held in place using a delivery device 120 or other tethering device.

a. Inflation/Deflation Features of Balloon Devices

FIG. 3 illustrates a transverse cross-sectional view through the balloon body 102 of the balloon device 100 as taken along section line 4-4 in FIG. 1. In this aspect, the balloon device 100 is formed from a thin flexible outer membrane 202. The outer membrane 202 may be sealed to the inner cylinder 204 at the proximal end 104 and at the distal end 108. Together, the outer membrane 202 and the inner cylinder 204 enclose a toroidal volume 206 that may enlarge and shrink as the balloon device 100 is inflated and deflated.

The inner cylinder 204 further encloses a cylindrical internal volume 208 that opens to the proximal opening 106 and the distal opening 110 at opposed ends. In an aspect, a delivery device 210 may be situated within the internal volume 208. In this aspect, the delivery device 210 may provide a means of situating the balloon device 100 upstream of the clot 116 as illustrated in FIG. 1. The delivery device 210 may further provide pneumatic pressure to inflate and/or deflate the balloon device 100. Other equipment may also be included or connected to the delivery device 210 including, but not limited to flow measurement devices, pressure sensors, temperature sensors, clot ablation or dissolving devices, and additional conduits through which additional substances may be introduced into the region of the lumen 112 situated downstream of the balloon device 100. Non-limiting examples of additional substances include: oxygenating compounds, nutrients, compositions for the treatment of the afflicted region downstream of the balloon device 100, clot-dissolving compounds, vascular dilation compounds, vascular constriction compounds, and any other suitable substance. A more detailed description of the delivery device 210, its associated equipment, and uses are described in detail herein below.

The balloon device 100 may be constructed from any suitable semi-compliant material known in the art. Non-limiting examples of suitable semi-compliant material include ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In another aspect, if the osmotic movement of fluid in or out of the balloon device 100 is desired, at least a portion of the balloon device 100 may be incorporated from a semi-permeable material including, but not limited to urethane. In various aspects, as described in detail herein below, a particular portion of the balloon device 100 incorporates a semi-permeable material in order to achieve any one of a variety of advantageous properties in use.

Figures 4A, 4B:
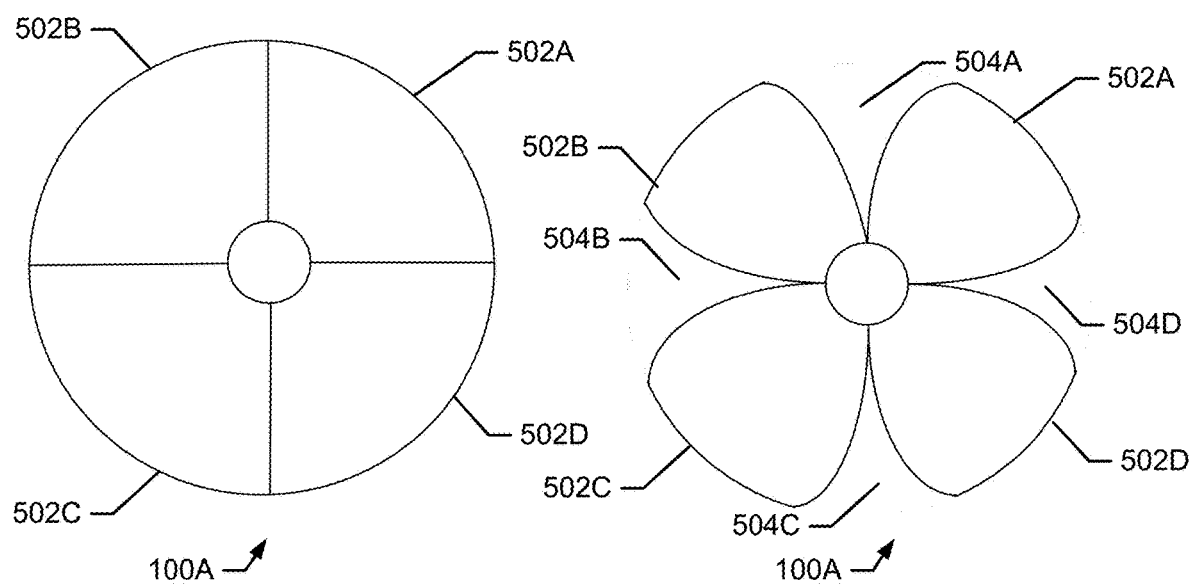
FIGS. 4A-4B are transverse cross-sectional views of the toroidal volume of a balloon device subdivided into four lobes.

In other aspects, the balloon device 100 may comprise alternative designs, resulting in different properties, in particular as related to the changes in cross-sectional area to reduce the occlusion factor. In the balloon device 100 illustrated in FIG. 1 and FIG. 2, the vessel flow 118 moves through a space formed between the vessel wall 114 and the balloon body 102 when the balloon device 100 is deflated. In another embodiment, illustrated in FIGS. 4A and 4B, which are transverse cross-sections of the toroidal volume of the balloon device 100A, the toroidal volume may be subdivided into two or more lobes; four lobes 502A-502D are illustrated in FIGS. 4A and 4B. When the balloon device 100A is inflated, as illustrated in FIG. 4A, the lobes 502A-502D are pressed tightly against each other, filling the entire cross-sectional area of the lumen of the vessel (not shown) and resulting in an occlusion factor of about 100%. When the balloon device 100A is deflated, as illustrated in FIG. 4B, the lobes 502A-502D may be designed to separate at their respective contact surfaces, forming channels 504A-5040 through which the vessel flow (not shown) may pass.

Figure 5A:
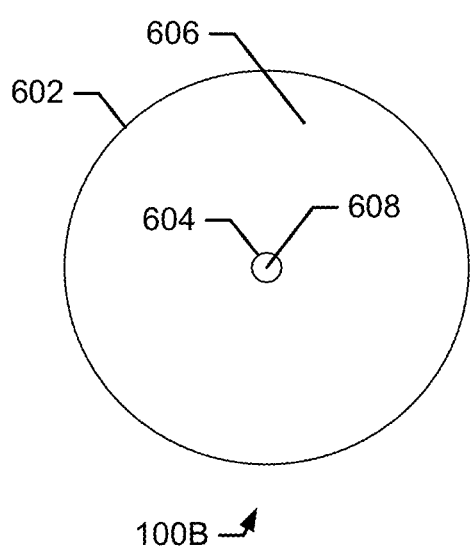
FIGS. 5A-5B are transverse cross-sectional views of a central passage formed by the deflation of a balloon device.
Figure 5B:
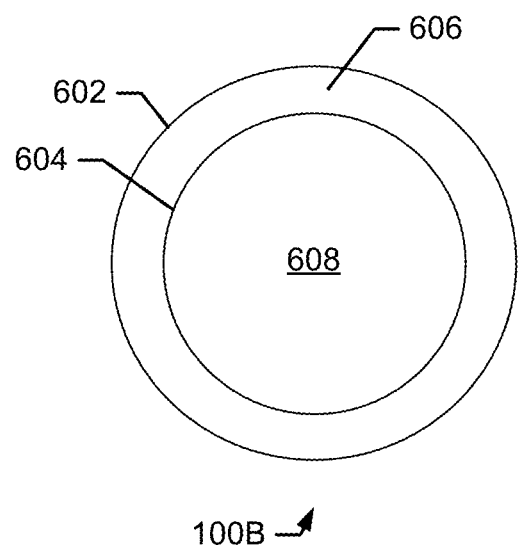

In an additional aspect, as illustrated in FIGS. 5A and 5B which are transverse cross-sections of the balloon device 100B, the balloon device 100B may be designed such that a central passage is formed by the deflation of the balloon device 100B. As illustrated in FIG. 5A, the inflated balloon device 100B includes a toroidal volume 606 bounded by an outer membrane 602 and an inner membrane 604. The inner membrane 604 encloses in inner lumen 608 which is essentially closed when the balloon device 100B is fully inflated, resulting in an occlusion factor of essentially 100%. When the balloon device 100B is deflated, as illustrated in FIG. 5B, the inner membrane 604 expands toward the outer membrane 602, thereby dilating the inner lumen 608. This inner lumen 608 may function as a conduit to carry vessel flow (not shown) into the region of the vessel downstream of the balloon device 1008, resulting in an occlusion factor of less than 100%.

b. Balloon Devices with Biodegradable Coatings

Figure 6A:
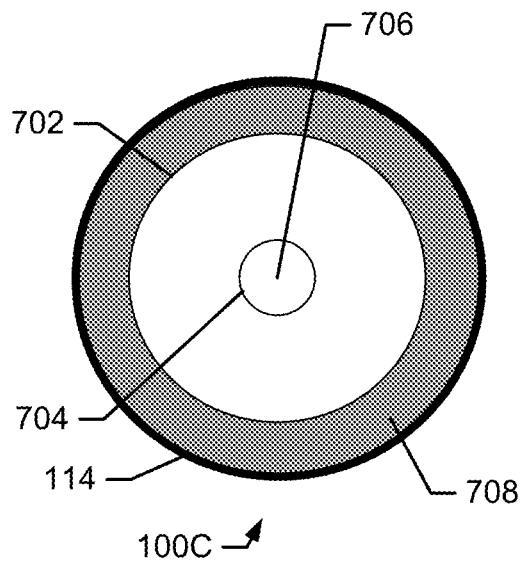
FIGS. 6A-6B are transverse cross-sectional views of an outer coating attached to the outer membrane of a balloon device.
Figure 6B:
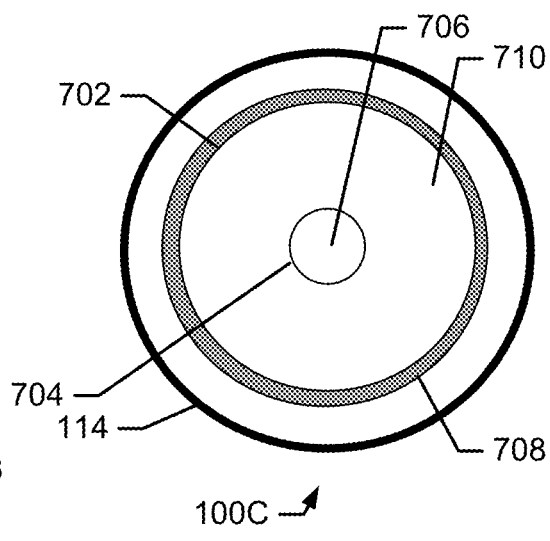

In yet another aspect, the balloon device 100C, illustrated in FIGS. 6A and 6B as transverse cross-sections, may include an outer coating 708 attached to the outer membrane 702 of the device 100C. In this aspect, the central volume 706 enclosed by the outer membrane 702 and the inner membrane 704 may remain relatively unchanged during the treatment using the balloon device 100C. However, the outer coating 708 may be constructed of a material that may spontaneously biodegrade under the physical and chemical conditions characteristic of the vessel 114 in which the balloon device is situated in one aspect. In another aspect, the outer coating 708 may incorporate a material that biodegrades upon exposure to a separate biodegrading agent introduced into the vessel 114. Regardless of the proximate cause of the biodegrading of the outer coating 708, the reduced cross-sectional area occupied by the balloon device 100C forms a toroidal space 710 between the outer layer 708 and the vessel 114 that allows for vessel flow into the lumen volume of the vessel situated downstream from the balloon device 100C.

Figure 6C:
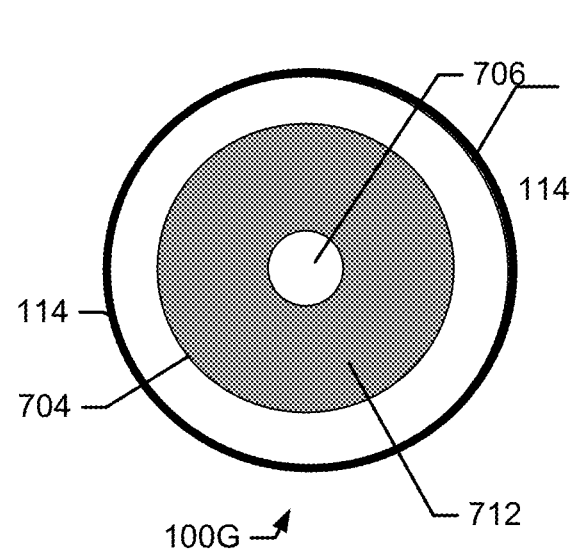
FIGS. 6C-6D are transverse cross-sectional views of an inner coating attached to the inner membrane of a balloon device.
Figure 6D:
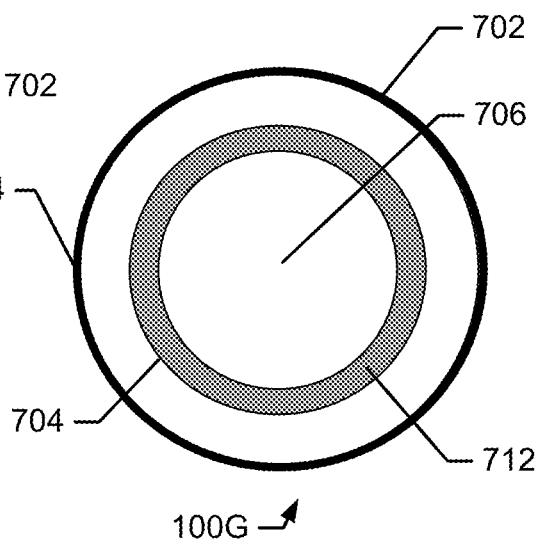

FIGS. 6C and 6D are transverse cross-sections of a balloon device 100D in another aspect. In this aspect, the balloon device 100G may be a cylindrical shell that maintains contact between the vessel 114 and the outer membrane 702 of the device 100G. An inner coating 712 may be attached to the inner membrane 704 of the device 100G. The inner coating 712 may reduce the extent of the volume 706 enclosed by the inner membrane 704. In a manner similar to the outer coating 708 described herein previously, the inner coating 712 may be constructed of a material that may spontaneously biodegrade under the physical and chemical conditions characteristic of the vessel 114 or upon exposure to a separate biodegrading agent introduced into the vessel 114. The biodegradation of the inner coating 712 results in an increase of the extent of the volume 706 enclosed by the inner layer 704, thereby allowing for vessel flow through the volume 706.

c. Osmotically Active Liquids of Balloon Devices

In one aspect, the balloon device 100 may be introduced by delivery device that includes a guide wire situated within an inner lumen of a multi-lumen catheter. The enclosed volumes of the balloon device 100 may be filled with a liquid introduced by an outer lumen of catheter to inflate the device 100. Any suitable incompressible liquid may be used to inflate the devices. Non-limiting examples of liquids suitable for inflating the balloon devices include: saline solution, plasma, whole blood, hydrophilic compounds, dopamine, papaverine, oxygenated fluids, TPA (Tissue Plasminogen Activator) and any other suitable incompressible fluid.

In an aspect, the concentration of the liquid introduced into the device 100 may be selected to be hyperosmotic, isoosmotic, or hypoosmotic relative to the surrounding blood within the vessel in which the device 100 is situated. In this aspect, if the outer membrane of the balloon device is constructed of a semipermeable material including, but not limited to, a urethane material, the introduction of the liquid into the device 100 may result in the passive movement of fluid into or out of the balloon device 100, depending on the tonicity of the liquid inside the device 100. In an aspect, the tonicity of the liquid inside the device 100 may be selected to result in a net movement of fluid into the balloon device, thereby passively maintaining the device 100 in an inflated configuration. In another aspect, the tonicity of the liquid inside the device 100 may be selected to result in a net movement of fluid out of the balloon device 100. In this aspect, the net movement of fluid out of the device 100 may be used as a passive mechanism by which vessel flow is reestablished in the vessel. As the fluid is driven from the device 100 by the osmotic gradient, the volume of the device 100 may subsequently shrink gradually over time, resulting in a slowly decreasing occlusion factor and the gradual reestablishment of vessel flow. The rate of transition to full physiological flow conditions in the vessel may be specified in part by the degree of tonicity of the liquid introduced into the balloon device 100.

In addition to passively reintroducing vessel flow, the passive movement of fluid out of the balloon device in this aspect may be further exploited to deliver compounds to the region in which the device is situated. In another aspect, the liquid introduced into the device 100 may further include one or more additional dissolved compounds including, but not limited to, active pharmaceutical compounds, oxygen-bearing compounds, nutrients, clot-dissolving compounds, and other suitable additional compounds. In order to deliver the one or more dissolved compounds to the desired region within the vessel, the balloon device may incorporate additional design features to implement the movement of fluid out of the device within specified regions of the device 100.

Figure 7:
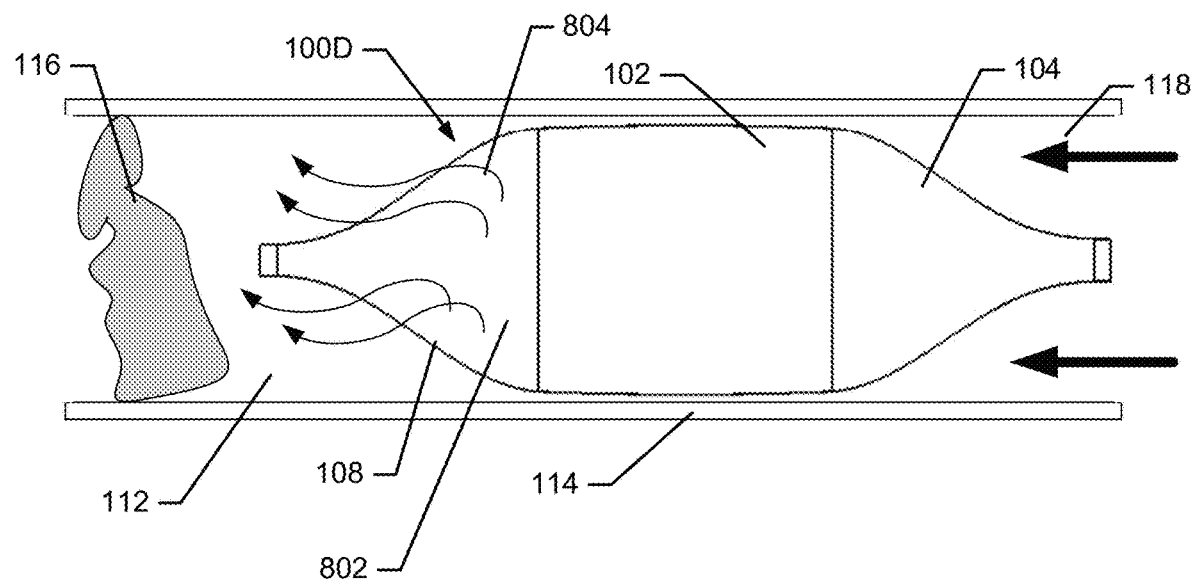
FIG. 7 is a longitudinal cross-sectional view of a balloon device constructed incorporating semi-permeable material on the distal end and a non-permeable material on the proximal end and balloon body.

For example, as illustrated in the longitudinal cross-sectional view of FIG. 7, the balloon device 100D may be constructed using a semi-permeable material such as urethane on the distal end 108, and using a non-permeable material on the remaining balloon body 102 and proximal end 104 portions of the device 100D. If the device 100D is filled with a liquid 802 having a tonicity that results in the net movement of fluid out of the device 100D, the construction of the device 100D limits the outward movement of fluid 802 to the distal end 108. If a dissolved compound 804 is included in the liquid 802, this dissolved compound 804 may be carried by the moving fluid 802 preferentially to the region of the lumen 112 situated downstream of the device 100D. For example, if the dissolved compound was a clot-dissolving compound, the device 100 may function to dissolve the clot 116 as well as to protect the lumen 112 and vessel wall 114 from potentially harmful elevated pressures and flow speeds. In another embodiment, the net movement out of the device 100D may be driven by increased hydrostatic pressure within the device 100D in addition to or instead of by osmotic pressure.

Figure 12:
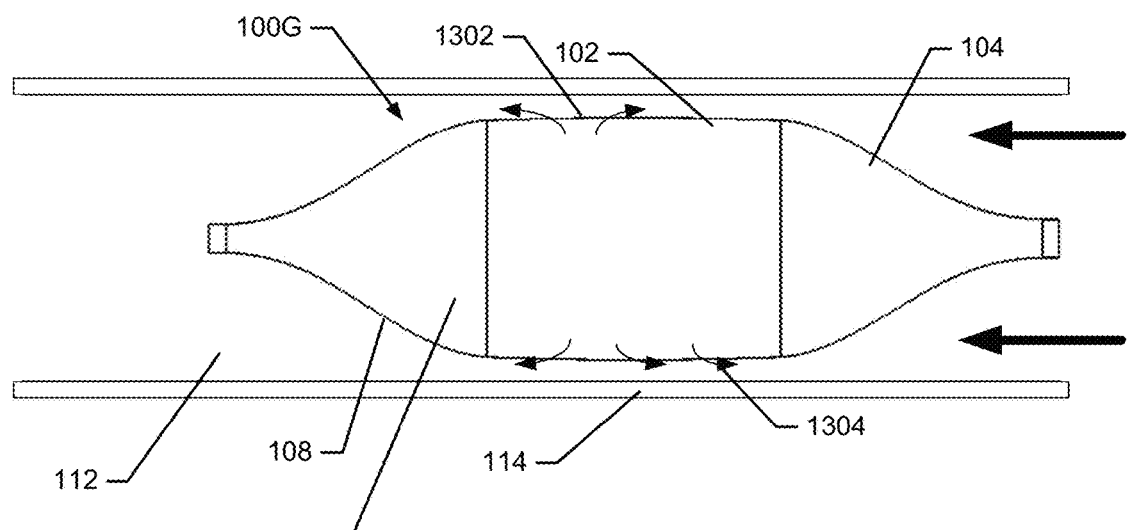
FIG. 12 is a longitudinal cross-sectional view of a balloon device constructed using a semi-permeable material situated around the perimeter of the balloon body.

In another aspect, the balloon device 100 may be constructed using a semi-permeable material including, but not limited to, urethane situated around the perimeter 1302 of the balloon body 102 as illustrated in FIG. 12. In this aspect, if the tonicity of the fluid introduced into the balloon device 100G results in a net outward movement of fluid from the device 100G, the expelled fluid 1304 may be situated in the gap between the perimeter 1302 of the balloon body and the vessel wall 114. Without being limited to any particular theory, this fluid movement may inhibit the adhesion of the balloon body 102 to the vessel wall 114 and/or inhibit the formation of thrombi within this area of contact. If the liquid 802 introduced into the balloon device 100G further includes a dissolved anti-adhesion compound in an aspect, the fluid movement may deliver the anti-adhesion compound between the perimeter 1302 and vessel wall 114, further inhibiting adhesion and/or clot formation. In another embodiment, the fluid movement out of the device 100G may result from elevated hydrostatic pressure within the device 100G, in addition to or instead of from osmotic pressure.

d. Multi-Balloon Devices

In an aspect, the implanted vessel flow control device may be a multi-balloon device. In one aspect, the multi-balloon device may include an upstream balloon and at least one downstream balloons situated in the vessel downstream of the afflicted area. For example, within a vessel that bifurcates into two downstream branches, the upstream balloon may be situated upstream of the bifurcation, and each of downstream balloons may be situated within a branch of the vessel downstream of the bifurcation point.

Figure 8:
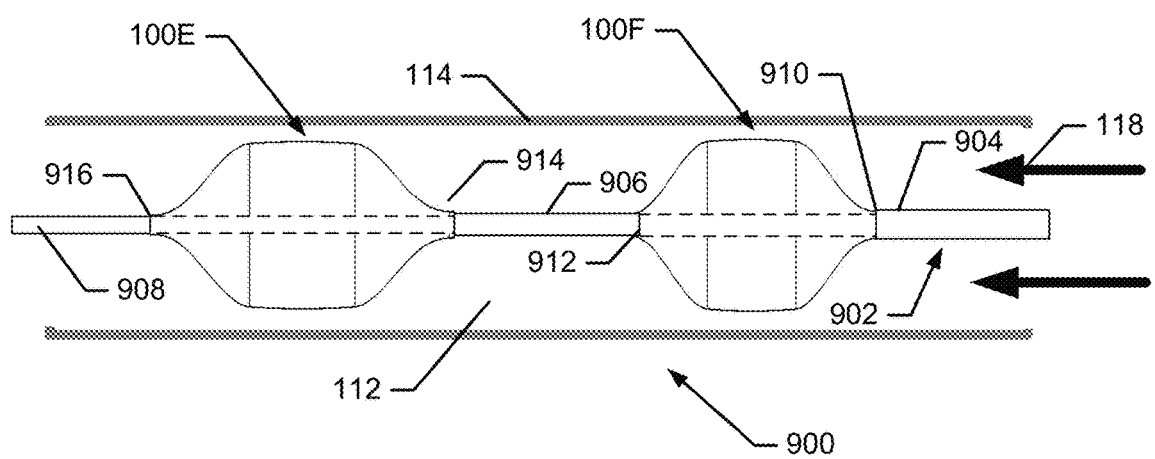
FIG. 8 is a longitudinal cross-sectional view of a two-balloon device.

As illustrated in FIG. 8, a two-balloon device 900 may include two balloons 100E and 100F similar in design to the single balloon devices 100 described herein previously. In this aspect, the two balloons are arranged sequentially along the length of a multi-segmented catheter 902 that includes three segments: a large-diameter segment 904, an intermediate diameter segment 906, and a small diameter segment 908. The small diameter segment 908 nests within the intermediate diameter segment 906 and the intermediate diameter segment 906 nests within the large-diameter segment 904. Thus, the segments 904, 906, and 908 may be coaxially arranged with each other such that the small diameter segment 908 is coaxially located within the intermediate diameter segment 906, which is coaxially located within the large diameter segment 904. The proximal end 910 of the multi-segment catheter 902, which includes all three segments 904, 906, and 908, extends out past the region at which the catheter 902 was introduced into the vessel lumen 112 of the patient. The proximal balloon 100F is sealed to the large-diameter segment 904 at location 906 and is further sealed to the intermediate diameter segment 906 at location 912. The distal balloon 100E is sealed to the intermediate diameter segment 906 at location 914 and is further sealed to the small diameter segment 908 at location 916. In this aspect, the two balloons 100E and 100F may be separated by a distance ranging from about 1 inch to about 3 inches.

With this arrangement, the proximal balloon 100F may be inflated or deflated by introducing or removing a fill liquid as described herein above via a fluid pathway defined between an outer circumferential surface of the intermediate-diameter segment 906 and an inner circumferential surface of the large-diameter segment 904. Similarly, the distal balloon 100E may be inflated or deflated by introducing or removing a fill liquid via a fluid pathway defined between an outer circumferential surface of the small-diameter segment 908 and an inner circumferential surface of the intermediate diameter segment 906. In this aspect, each balloon 100E or 100F is hydraulically independent of the other balloon, providing the ability to inflate or deflate one balloon device independently of the other device. In use, this hydraulically independent design may result in at least several useful features for the device 900.

Figure 10:
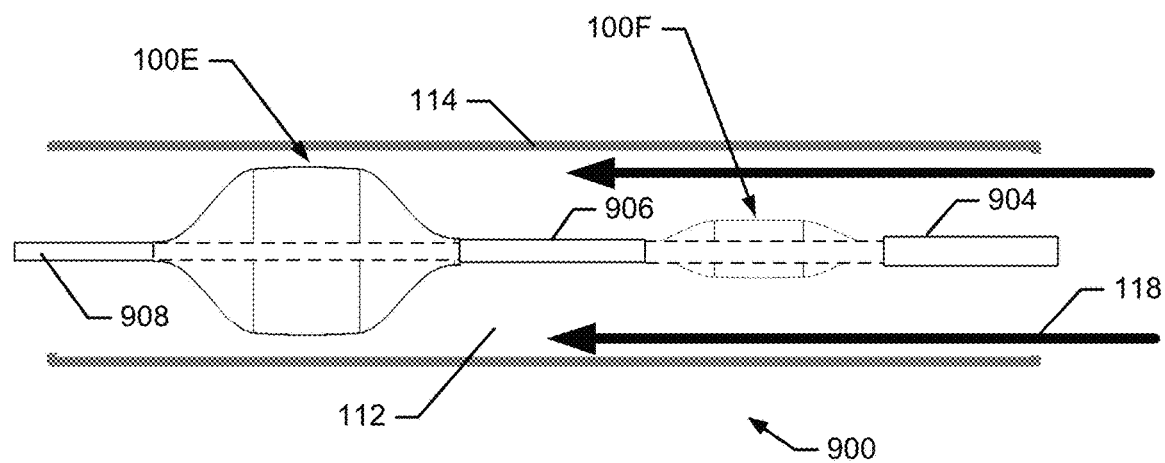
FIG. 10 is a longitudinal cross-sectional view of a two-balloon device with the upstream balloon deflated and the downstream balloon inflated.

In one aspect, illustrated in the longitudinal cross-sectional view of FIG. 10, the proximal balloon 100F may be deflated while the distal balloon 100E is maintained in an inflated configuration. This configuration of the device 900 may provide access to the region 112 downstream of the proximal balloon 100F, which may include the afflicted region of the patient containing a clot or other abnormality. In this configuration, the afflicted region of the lumen 112 may be rendered accessible to additional instruments such as delivery devices, or accessible to contact by treatment compounds such as clot-dissolving substances, by oxygenated blood and/or nutrients, and/or any other suitable instrument or compound. By maintaining the distal balloon 100E in an inflated configuration, the upstream flow 918 may contact the afflicted region 112 without exposing the afflicted region 112 to high flow rates. In another aspect, the configuration illustrated in FIG. 10 may be used to prevent the formation of thrombi within the contact area between the proximal balloon 100F and the vessel wall 114.

Figure 11:
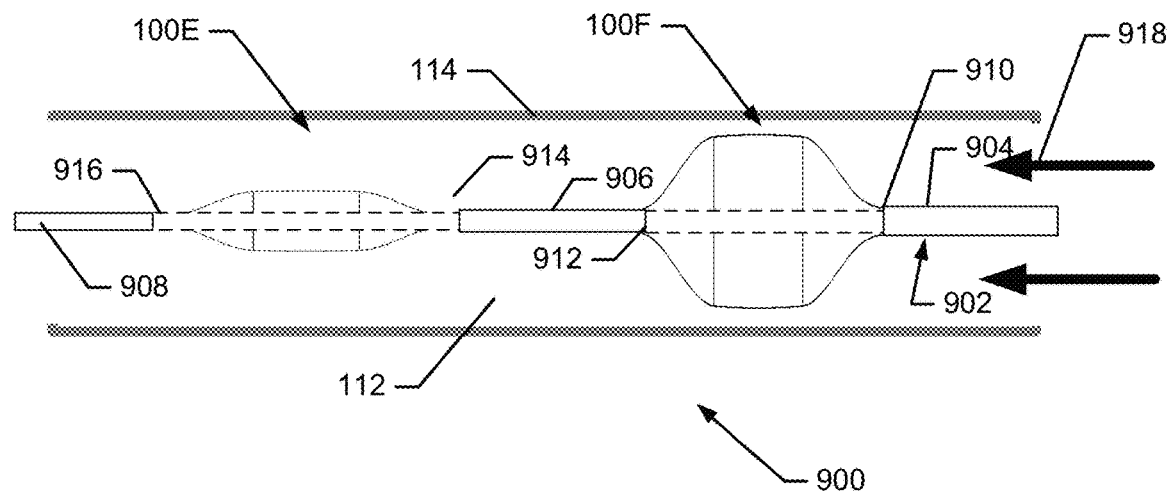
FIG. 11 is a longitudinal cross-sectional view of a two-balloon device with the downstream balloon deflated and the upstream balloon inflated.

In another aspect, illustrated in the longitudinal cross-sectional view of FIG. 11, the distal balloon 100E may be deflated while the proximal balloon 100F is maintained in an inflated configuration. This configuration of the device 900 may provide fluidic contact between the afflicted region 112 and the vessel region downstream of the distal balloon 100E. In this configuration, the afflicted region 112 and surrounding tissues may be rendered accessible to additional instruments such as additional delivery devices introduced into the vessel lumen downstream of the device 900, or accessible to contact by treatment compounds such as clot-dissolving substances, by oxygenated blood and/or nutrients, and/or any other suitable instrument or compound. By maintaining the proximal balloon 100F in an inflated configuration, the upstream flow 918 remains sheltered from the physiological blood flow, thereby preventing the exposure of the afflicted region of the lumen 112 to the elevated physiological pressures and flow rates. In another aspect, the configuration illustrated in FIG. 11 may be used to prevent the formation of thrombi within the contact area between the distal balloon 100E and the vessel wall 114.

In addition to the advantages of the dual-balloon device 900 described herein above, this arrangement may further enhance the degree of control over the flow rate and pressure experienced within the afflicted region 112 of the vessel. For example, the distal balloon 100E may be differentially inflated or deflated relative to the proximal balloon 100F in order to increase or decrease the pressure experienced with the afflicted region 112. Other combinations of differential inflation or deflation of the balloons 100E and 100F are possible and may result in additional degrees of enhanced control over the flow conditions experienced by the afflicted region 112 of the vessel.

In another aspect, the small diameter segment 908 extends uninterrupted from the upstream side to the downstream side of the device 900, as illustrated in FIG. 8. As a result, the small diameter segment 908 provides a bypass of the device 900 from the proximal side to the distal side through which a variety of substances may be provided to the vessel downstream of the device 900. For example, the small diameter segment 908 may be used to deliver one or more additional substances including, but not limited to, oxygenated blood, nutrients, artificial blood, therapeutic compounds, and any other suitable compound to the region of the vessel downstream from the device. Because the device 900 typically completely blocks vessel flow for at least a portion of its working lifetime, the vessel and tissues downstream of the device 900 may suffer oxidative, nutritive, and other physiological stresses due to the treatment of the patient using the device 900. By introducing the one or more additional substances to the region of the vessel situated downstream of the device 900, the vessel in this region and its associated tissues may be maintained in a physiologically viable state during the course of treatment using the device 900.

e. Balloon Instrumentation

In another aspect, the balloon devices 100 and/or 900 described herein above may additionally include instrumentation to measure relevant physical and chemical conditions in the vessel regions upstream, immediately adjacent, and/or downstream of the device 100 or 900. Non-limiting examples of suitable physical and chemical conditions include: flow rate, pressure, temperature, pH, hematocrit, platelet count, electrical activity, cytokine, glucose, oxygen, carbon dioxide, and other relevant compound concentrations. Any known instrumentation may be incorporated into the balloon devices 100 and/or 900, as long as the selected instrumentation is biocompatible and of suitable size for introduction into the vessel of the patient.

Non-limiting examples of suitable instrumentation for incorporation into the devices 100 and/or 900 in various aspects include thermocouples for measuring temperature, piezoelectric pressure sensors, heated velocity sensors, and any other known suitable miniature sensor. For example, a heated velocity sensor may include a heated or cooled strip of material upon which one or more strain gages are mounted. The flow rate may be determined by assessing the effect of conductive heating or cooling induced by the vessel flow on the strain gage resistance.

In various aspects, the instrumentation may be mounted at any location relative to the balloon device without limitation. In one aspect, two pressure sensors may be situated such that one pressure sensor measures the pressure upstream of the balloon device 100 or 900, and the second pressure sensor measures the pressure downstream of the balloon device. A comparison of the upstream and downstream pressures may provide an indication of the flow vessel flow conditions. For example, if the upstream pressure sensor indicates a higher pressure than the downstream pressure sensor, this differential may be interpreted as confirmation that the vessel flow is significantly occluded by the device 100 or 900. In this example, an equalization of the upstream and downstream pressures may be expected as the occlusion diminishes.

ii. Stent Devices

Figure 13:
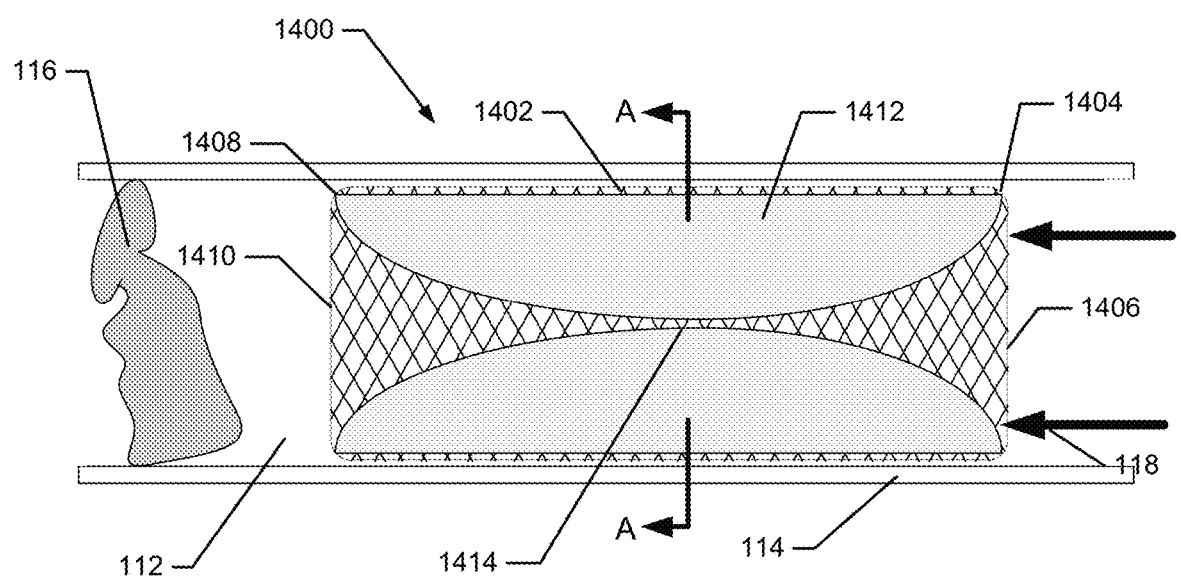
FIG. 13 is a longitudinal cross-sectional view of a stent device.

In another aspect, the vessel flow control device may be a stent device. FIG. 13 is a longitudinal cross-section of a stent device 1400 in an aspect. The stent device 1400 may include a stent body 1402 that has a roughly hollow cylindrical shape when deployed. The stent body 1402 may include a proximal end 1404 containing a proximal opening 1406, and a distal end 1408 containing a distal opening 1410.

In an aspect, the stent 1400 may be constructed using any material known to be suitable for stent construction including, but not limited to stainless steel; NITINOL; bio-resorbable materials including PGA, PDS, PGA-PCL, and PLLA; biodegradable materials including enteric coating materials and hydrogel materials; PEEK; any other known stent materials, and any combination thereof.

The stent 1400 may be situated within a lumen 112 of a vessel 114 upstream relative to a clot 116 or other obstructive structure; upstream may be defined by the direction of the flow 118 in the lumen 112. In another aspect the stent 1400 may be situated over the clot 116 or other obstructive structure; in this aspect, the stent 1400 may compress the clot 116 against the wall of the vessel 114. When fully deployed, the stent body 1402 may expand to a diameter essentially equal to the diameter of the vessel lumen as illustrated in FIG. 13.

In addition, the stent 1400 may include an occlusive element 1412 to impede the vessel flow 118 to a predetermined degree, resulting in a predetermined occlusion factor. The occlusive element 1412 may be any structural feature within the stent 1400 capable of occluding the vessel flow 118. As illustrated in FIG. 13, the occlusive element 1412 may be an approximately hourglass-shaped solid structure that narrows to a channel 1414 through which the vessel flow may pass. In an aspect, the occlusive element 1412 may be fabricated from a biodegradable material capable of biodegrading and/or resorbing over a predetermined period, resulting in a gradual decrease of the occlusion factor, and a commensurate increase in vessel flow, in accordance with a predetermined schedule. In another aspect, the occlusive element 1412 may be fabricated from a semipermeable membrane filled with an osmotically active fluid that gradually releases fluid into the vessel, resulting in the gradual widening of the channel 1414, thereby decreasing the occlusion factor of the stent 1400. In another aspect, the entire stent 1400 may be constructed from at least one biodegradable material. In this aspect, the entire stent 1400 may partially or completely biodegrade and/or resorb over time.

Figure 14:
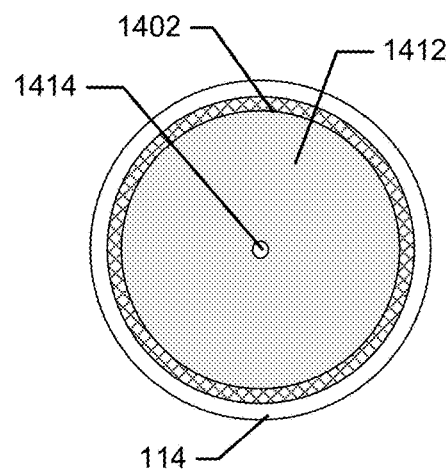
FIG. 14 is a transverse cross-sectional view of a stent device.
Figure 15:
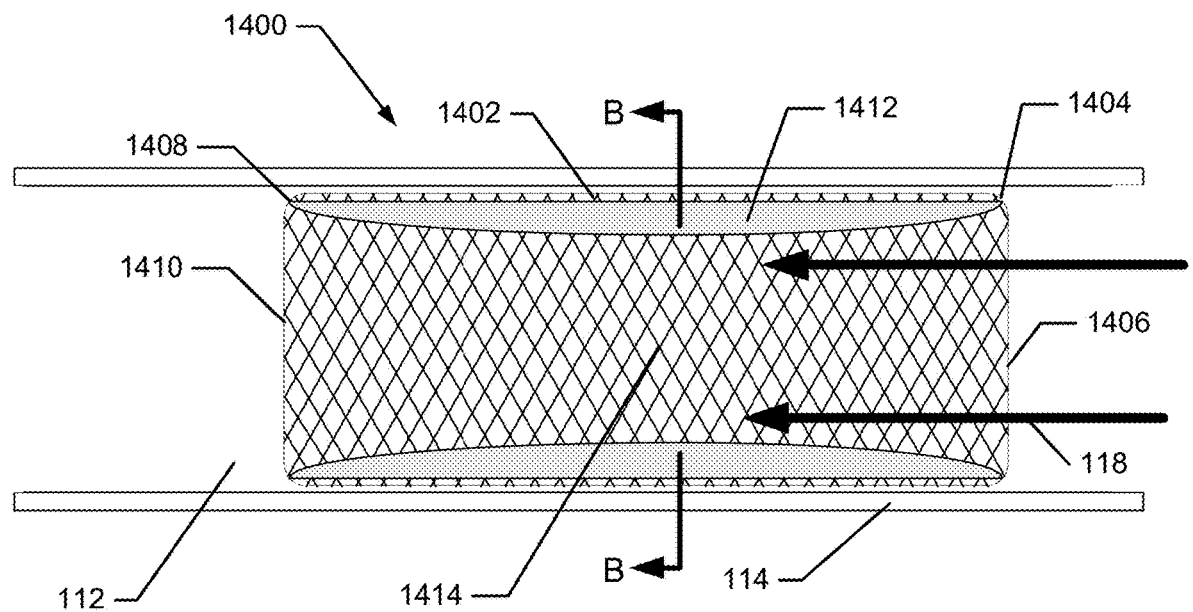
FIG. 15 is a longitudinal cross-sectional view of a stent device in an open-flow configuration.

FIG. 14 is a transverse cross-sectional view of the stent 1400 taken at section A-A as denoted in FIG. 13. FIG. 14 illustrates the occlusive element 1412 situated within the stent 1402 as well as the channel 1414 formed within the center of the occlusive element 1412. In this configuration, the stent device 1400 has an occlusion factor of about 100% or substantially 100%, and no flow or substantially no flow may pass the stent body 1402. FIG. 15 is a longitudinal cross-section of the stent 1400 illustrated in FIG. 13 with reduced occlusive element 1412 and widened channel 1414. In this configuration, the occlusion factor of the stent device 1400 may be significantly reduced to a level as low as about 5%, thereby allowing a significantly higher vessel flow 118 through the vessel lumen 112. Detailed descriptions of various aspects of the design and characteristics of the occlusive element 1412 are provided herein below.

Referring back to FIG. 13, if the clot 116 is removed from the lumen 112, the flow 118 through the vessel 114 may be reestablished up to physiological flow speeds and flow pressures. In an aspect, the stent 1400 may be gradually collapsed as illustrated in the longitudinal cross-sectional view of FIG. 15, causing a reduction in the diameter of the stent body 1402 such that the cross-sectional area of the stent body 1402 no longer fills the cross-sectional area of the lumen 112, resulting in an occlusion factor of less than 100%. In this configuration, the flow 118 within the vessel may pass the stent body 1402 in the annular space formed between the stent body 1402 and the lumen 112; this establishment of flow in the vessel 114 results in a rise in the flow rate and pressure downstream of the stent device 1400. The gradual collapse of the stent 1400 may be implemented in a passive structure that spontaneously collapses over time, or the gradual collapse of the stent may be actively controlled by a practitioner in various aspects. For example, the stent 1400 may be constructed from NITINOL memory wire in a configuration capable of collapsing a predetermined amount in response to a physical factor such as an electrical current or transfer of thermal energy or a mechanical input.

Figure 16:
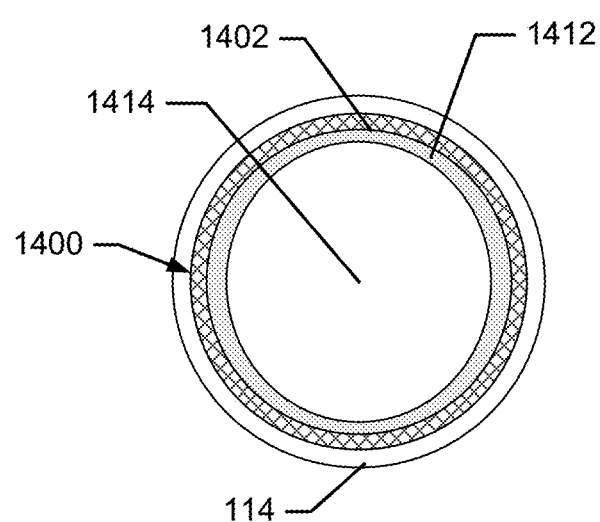
FIG. 16 is a transverse cross-sectional view of a stent device with a biodegraded occlusive member.

In another embodiment as shown in FIG. 16, which is a longitudinal cross-sectional view of the stent 1400 illustrated in FIG. 14 in a biodegraded condition, the occlusive element 1412 may biodegrade to produce an enlarged channel 1414 within the occlusive element 1412 through which vessel flow may travel. As the channel 1414 gradually widens, the occlusion factor decreases proportionally. In an aspect, the occlusive element 1412 may be designed to biodegrade at a steady and predetermined rate, resulting in a gradual increase in vessel flow velocity according to a predetermined schedule. In another aspect, the occlusive element 1412 may be formed into an expandable structure such as an iris-type structure, wherein the expandable structure is designed to slowly expand according to a predetermined schedule, resulting in the gradual increase of vessel flow through the stent 1400. The dissolution and/or expansion of the occlusive element may occur spontaneously, or in response to exposure to a physical and/or chemical agent that triggers the dissolution or expansion. In an aspect, the dissolution and/or expansion of the occlusive element 1412 may occur in response to exposure to an injected medium introduced into the vessel 114 upstream of the stent 1400.

In an aspect, the occlusive element 1412 may biodegrade over a period of time sufficient to allow for the healing of the vascular tissues injured by the clot 116. The rate at which the occlusive element 1412 biodegrades to reestablish flow within the vessel 114 may be specified using a variety of methods discussed in detail herein below.

In an aspect, the interior and exterior surfaces of the stent 1400 may be coated up to the full extent of the stent 1400 with a variety of coating materials including, but not limited to, biodegradable materials, resorbable materials, clot-dissolving materials, and any other known coating material suitable for use in an implantable stent design. In one aspect, the stent 1400 may be partially or fully coated to facilitate in the compression of a clot or other structure, resulting in the reestablishment of physiological vessel flow.

In another aspect, the occlusive element 1412 may incorporate biodegradable and/or bioresorbable materials in a configuration designed to biodegrade at a predetermined rate. In an aspect, the occlusive element 1412 may be constructed partially of biodegradable and/or bioresorbable materials with additional non-biodegradable structural elements such as cross members, a mesh, and/or a screen. In other aspects, the occlusive element 1412 may be constructed entirely of biodegradable and/or bioresorbable materials. The dimensions and design of the occlusive element 1412 may be selected based on one or more of at least several factors including, but not limited to the desired dissolution rate, the desired structural integrity of the stent 1400, the ease of deployment and collapse of the stent 1400 in use, and any other relevant factor.

iii. Hybrid Devices

In other additional aspects, the vessel flow control device may include any combination of any number of external flow control devices and implantable flow control devices without limitation. For example, the vessel flow control device may include an external flow control device such as an external clamp and an implantable flow control device such as a stent device. In another example, the vessel flow control device may include a stent device as well as a balloon device in combination.

II. Methods of Using Vessel Flow Control Device

The vessel flow control device may be used to treat an afflicted region of a patient using methods described herein below in various aspects. In one aspect, a vessel flow control device is situated in a vessel of a patient upstream of the afflicted region and configured to an occlusion factor of essentially 100%, resulting in the essentially complete obstruction of the vessel flow to the afflicted region. As the afflicted region recovers, the occlusion factor of the vessel flow control device may be gradually decreased, resulting in a gradual increase in vessel flow and/or vessel pressure in the afflicted region. This gradual decrease of the occlusion factor may be specified using any one of at least several control methods. Non-limiting examples of suitable control methods include: autonomous device-based adjustments such as the dissolution of obstructive materials in the device as described herein above; manual adjustment by a medical practitioner; automated adjustment of the vessel flow according to a predetermined schedule; and/or automated adjustment of the vessel flow based on commands from a feedback control system.

a. Treatment Algorithm

Figure 9:
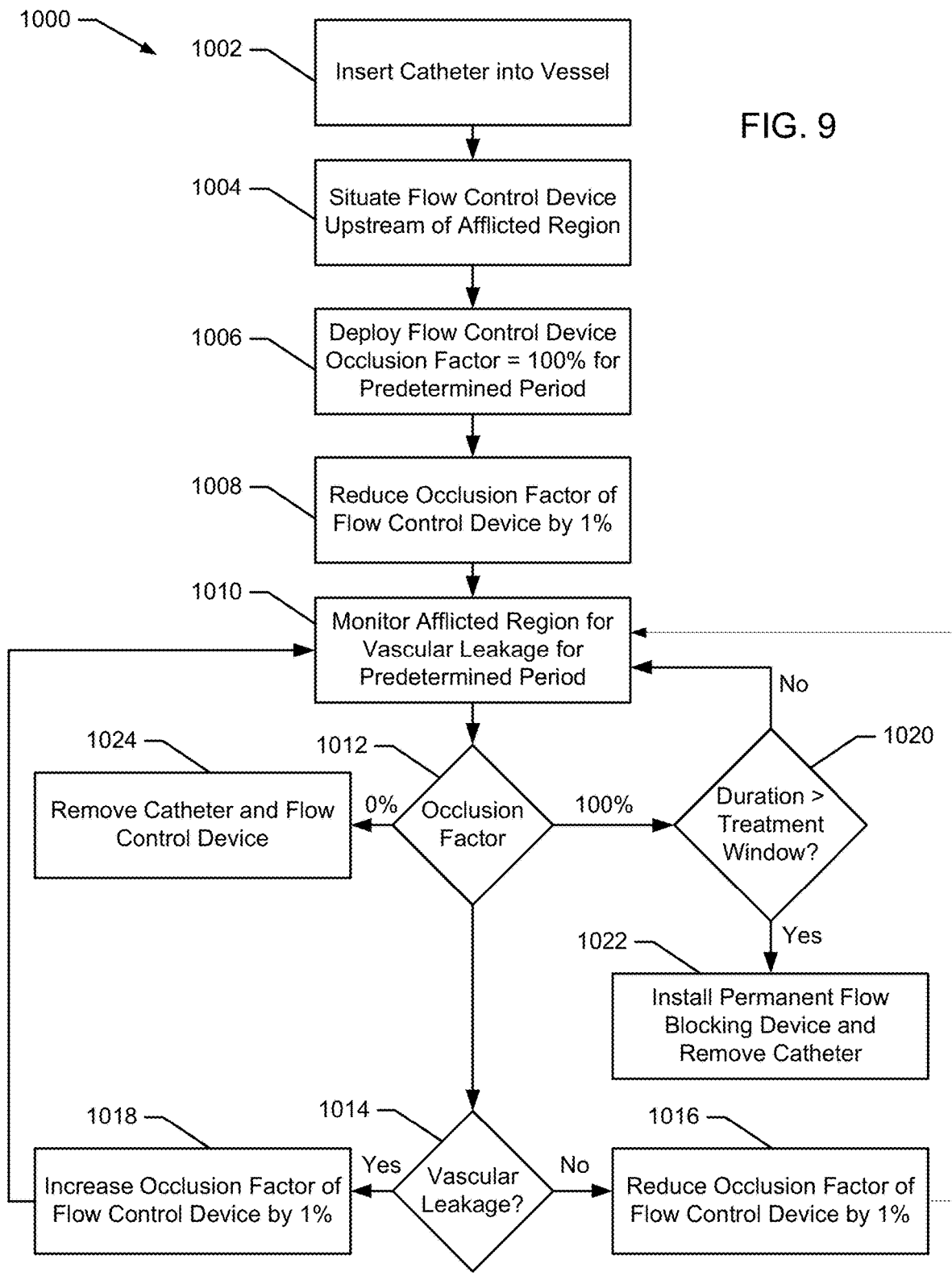
FIG. 9 is a flow chart diagram of a method of using a vessel control device to treat an afflicted region of a patient.

A procedure for treating an afflicted region of a patient using a vessel flow control device is provided in one aspect. A flowchart 1000 illustrating the steps of the procedure is provided in FIG. 9. In this aspect, a delivery device with the attached vessel flow control device may be inserted into the vessel of the patient at step 1002. After the delivery device has been inserted, the flow control device may be situated upstream of the afflicted region of the patient at step 1004. The flow control device may then be deployed to occlude the vessel and stop blood flow to the afflicted region. In this aspect, the flow control device may be deployed to an occlusion factor of about 100% for a predetermined time at step 1006. Once the flow control device has been completely deployed, the occlusion factor of the flow control device may be reduced by about 1% to restore some blood flow past the flow control device to the afflicted area at step 1008. The afflicted region may then be monitored for vascular leakage for a predetermined period, as shown in step 1010.

In this aspect, the occlusion factor and vascular leakage may be assessed and this information may be used to determine any adjustments to be made to the occlusion factor of the device to increase or decrease the flow to the vessel. If the occlusion factor is determined to be not equal to 100% or 0% at step 1012 and if there is no vascular leakage at step 1014, then the occlusion factor of the flow control device may be reduced by another 1% at step 1016 to increase the blood flow in the vessel. After the reduction in the occlusion factor, the afflicted region may again be monitored for vascular leakage at step 1010.

If the occlusion factor is not equal to 100% or 0% at step 1012 and if there is vascular leakage indicated at step 1014, then the occlusion factor of the flow control device may be increased by about 1% at step 1018 to decrease the flow through the vessel in order to stabilize the patient or treatment. Steps 1010, 1014, 1016 and 1018 are repeated until the occlusion factor reaches either 100% indicating irreparable vessel damage or 0%, indicating reestablishment of physiological flow in the vessel.

In this aspect, after step 1010, if the occlusion factor reaches 100% at step 1012, and the duration of treatment indicated at step 1020 is greater than a treatment window representing a maximum treatment time within which a favorable response is expected, then a permanent flow blocking device may be installed and the delivery device may be removed at step 1022. If the occlusion factor reaches 100% at step 1012, and the duration is not greater than the treatment window at step 1020, then the afflicted region may be monitored for vascular leakage for a predetermined period of time at step 1010 to assess whether the condition of the vessel is improved. If the occlusion factor reaches 0% at step 1012, then the vessel is indicated as healed, and the delivery device and the flow control device may be removed at step 1024.

c. Methods of Monitoring Blood Flow

In various aspects, the adjustments to the vessel flow rate during the treatment of an afflicted region of a patient may be influenced by measurements obtained to monitor the blood flow within the afflicted region. For example, measurements that detect vascular leakage within the afflicted region may indicate the need to decrease the vessel flow by increasing the occlusion factor of the device.

Blood flow in the vicinity of the vessel flow control device and vascular leakage may be monitored during treatment using any known method. Non-limiting examples of suitable methods for monitoring blood flow and vascular leakage include: angiogram, ultrasound, Doppler ultrasound, computed tomography (CT), magnetic resonance imaging (MRI), magnetic resonance angiography (MRA), heat transfer, patient neurological tests, and/or any other method of monitoring blood flow known in the art. In an aspect, an angiogram may be used to monitor blood flow by injecting a contrast medium from a delivery device such as a catheter and measure the rate of movement of the contrast medium down the vessel. Ultrasound may be used in an aspect to directly image blood flow or may be used as an ultrasonic flow meter by measuring the transit time between pulses from ultrasound transducers in opposite direction. In another aspect, Doppler ultrasound may utilize the change in pitch of reflected sound waves off of moving blood cells to measure blood flow. CT or computerized axial tomography (CAT) may be used with or without a contrast agent to measure blood flow by comparing sequential scans. In some aspects, CT and/or CAT may be used with xenon or positron emission tomography (PET) for enhanced imaging. In yet another aspect, MR may be used to track blood flow including, but not limited to, instant MRI, functional MRI, or MR angiography. The measurement of heat loss of a device in the blood stream may measure the flow of blood past the device in one aspect.

d. Control Methods

The occlusion factor of the vessel flow control device may be increased or decreased to control flow in vessels using any of the methods and structures described herein previously. Non-limiting examples of methods of controlling blood flow and the occlusion factor of the device include autonomous device-based adjustments, manual adjustments, programmable adjustments, and feedback control adjustments.

In an aspect, the vessel flow control device may incorporate features and materials that result in the gradual decrease in occlusion factor due to the intrinsic properties of the device 100. In an aspect, the flow control device 100 may be constructed of a material that may lose pressure or biodegrade at a constant rate, including, but not limited to, a biodegradable material, a porous material, urethane, or any other material known in the art. In another aspect, the flow control device 100 may be made of a material that may have an adjustable osmosis rate. In this aspect, various materials may be flushed over or inside the flow control device 100 to change the deflation rate and alter the occlusion factor. In an aspect, the pressure losses within the device may be used to alter the occlusion factor of the device as described herein previously.

Figure 17:
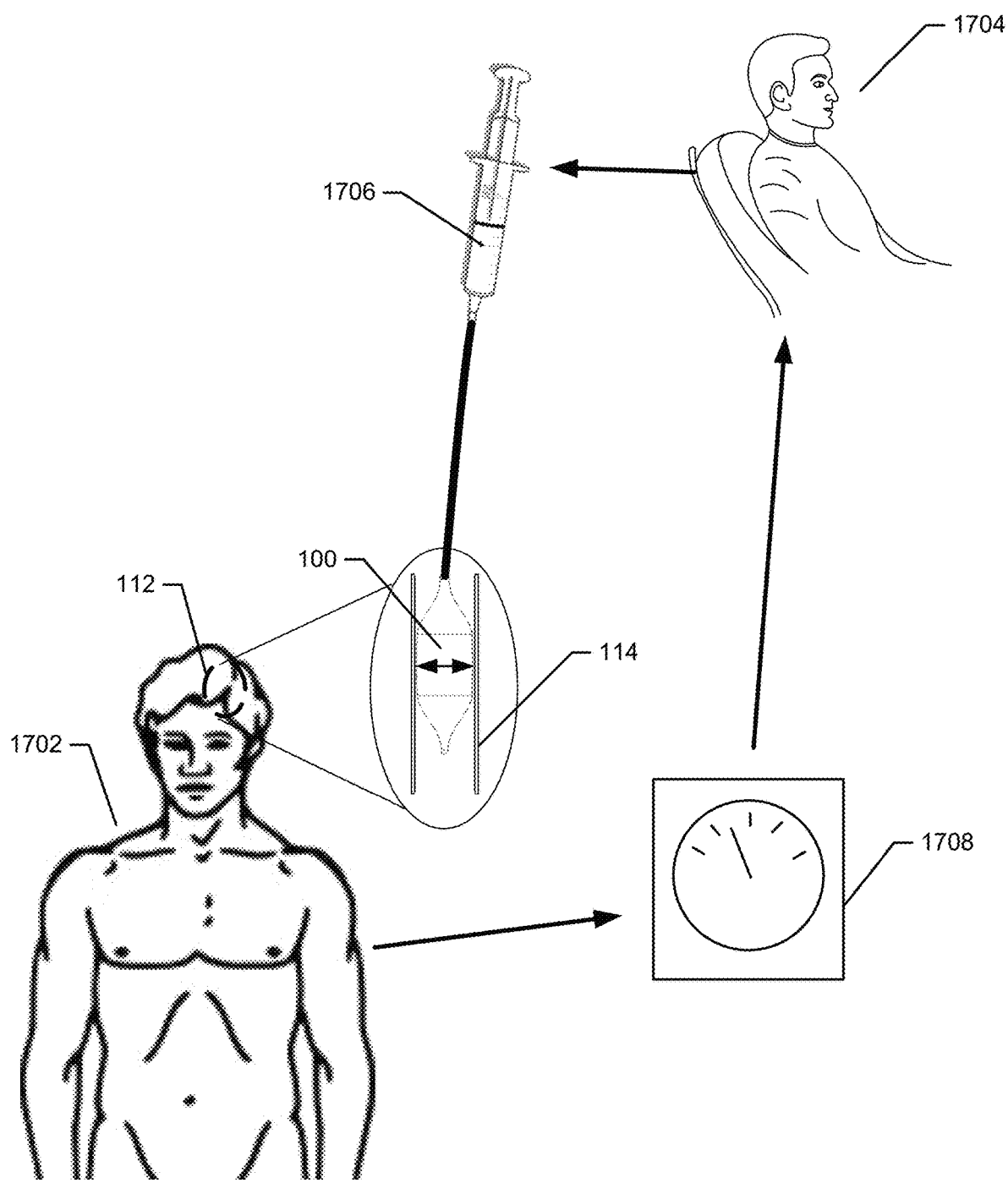
FIG. 17 is a schematic diagram of a method of manually controlling a vessel flow control device.

In another aspect, the occlusion factor of the device may be manually controlled. FIG. 17 is a schematic diagram illustrating the manual control of the occlusion factor of the vessel flow device 100 by a medical practitioner 1704. After the vessel flow control device 100 is situated within a vessel 114 upstream of an afflicted region 112 of a patient 1702, a medical practitioner 1704 may manually adjust the occlusion factor of the device 100 using a manual adjustment apparatus 1706 such as an adjustment syringe as illustrated in FIG. 17. The medical practitioner 1704 may monitor the vessel flow in the afflicted region 112 using one or more measurements 1708 described herein previously, such as ultrasound or MRI imaging.

For example, the medical practitioner 1704 may manually decrease the occlusion factor of the device 110 after observing measurements 1708 that indicate normal vessel flow in the afflicted area 112. This manual adjustment results in increased vessel flow through the afflicted region 112. The medical practitioner 1704 may continue to monitor the measurements 1708 and make additional manual adjustments to the occlusion factor of the device 100 using the manual adjustment apparatus 1706 as needed.

In this aspect, manual adjustment methods may include, but are not limited to, manipulating fine adjustment syringes and/or stop-cocks to control the decrease or increase of the occlusion factor of the flow control device 100. In another aspect, manual adjustment may use fixed rate/flow items to control the decrease or increase of the occlusion factor of the flow control device. The blood flow may change in this aspect by manually adjusting the constant leak rate of the flow control device, resulting in a constant increase or decrease in the occlusion factor of the flow control device. In another aspect, the blood flow may be controlled by the use of a manual flow, osmosis, or a leak rate device that may be attached to the flow control device to control removal of fluid from the flow control device to increase or decrease the occlusion factor.

Figure 18:
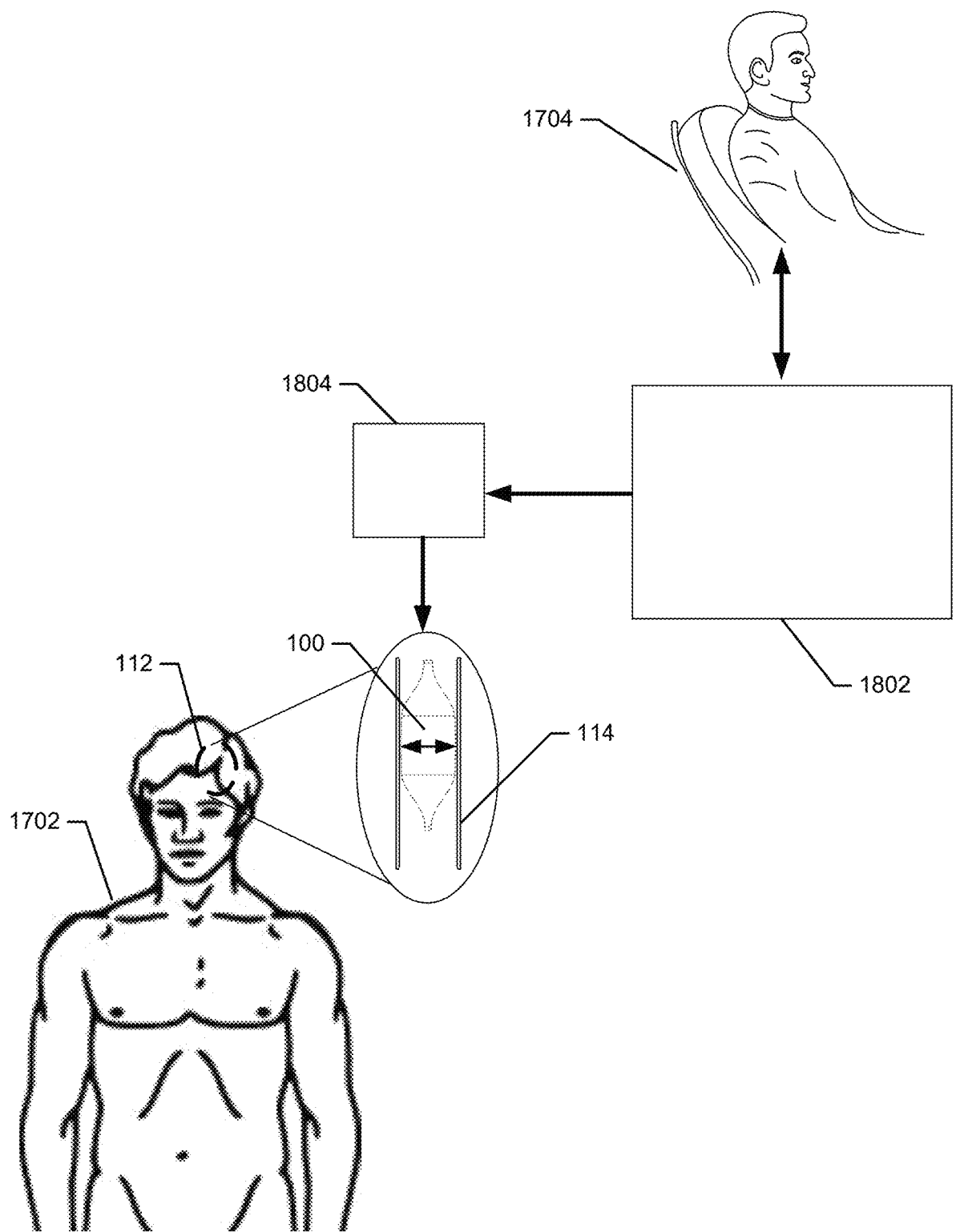
FIG. 18 is a schematic diagram of a method of controlling a vessel flow control device using an automated device.

A programmable device may be used to control blood flow and the increase or decrease of the occlusion factor of the flow control device in another aspect. FIG. 18 is a schematic diagram illustrating a method of controlling the occlusion factor of the vessel flow control device 100 using a programmable device 1802 in an aspect. In this aspect, the programmable device 1802 may send a series of control signals to an automated adjustment device 1804. In response to the series of control signals received from the programmable device 1802, the automated adjustment device may implement the adjustment of the occlusion factor of the device 100. In another aspect, the series of control signals generated by the programmable device 1802 may be specified, adjusted, and/or manually input into the programmable device 1802 by the medical practitioner 1402. For example, the medical practitioner 1402 may select a more gradual rate of adjustment implemented by the programmable device 1802.

The programmable device 1802 may include CPU, processors, and computer readable media that execute stored commands and/or algorithms to implement a series of adjustments to the occlusion factor of the vessel flow control device 100 according to a predetermined schedule. The programmable device 1802 may use a predefined adjustment rate that may follow a pre-stored rate of blood flow or pressure increase or decrease. In an aspect, the programmable device 1802 may follow a programmable but defined rate of change. A motorized syringe or other adjustment device 1804 may be used to increase or decrease the occlusion factor at a constant fixed rate in one aspect. An electronic syringe or adjustment device 1804 in an aspect may allow multiple pre-stored changes to stop and start a constant or fixed rate flow control device 100 to increase or decrease the occlusion factor.

In another embodiment, a feedback control system may be used to control the blood flow or pressure using feedback from measured signs and symptoms from the patient. In an aspect, external patient metrics may be used to automatically change the rate of increase or decrease of the occlusion factor of the flow control device and change the corresponding blood flow/pressure. In another aspect, internal vascular patient metrics and/or patient signs and symptoms may automatically change the rate of increase or decrease of the occlusion factor of the flow control device and change the corresponding blood flow/pressure.

Figure 19:
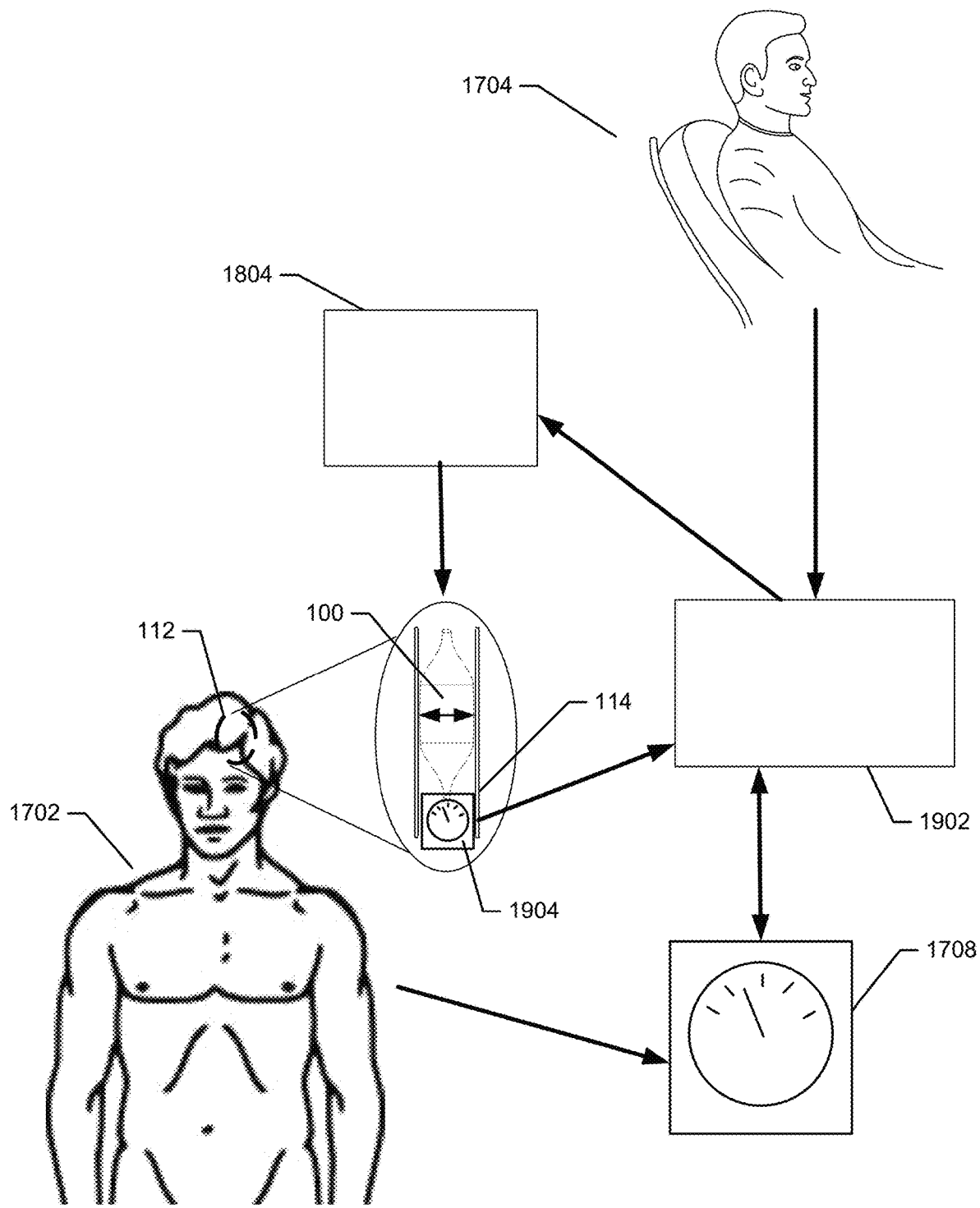
FIG. 19 is a schematic diagram of a method of controlling a vessel flow control device using a feedback control device.

FIG. 19 is a schematic diagram illustrating the control of the occlusion factor of the vessel flow control device 100 using a feedback control device 1902. The feedback control device 1902 may include CPU, processors, and computer readable media that execute stored commands and/or algorithms to implement a series of adjustments to the occlusion factor of the vessel flow control device 100 based on measured quantities related to blood flow within the afflicted area 112 as described herein above. For example, the feedback control device 1902 may execute stored instructions to implement a control algorithm similar to the algorithm described herein above and illustrated in FIG. 9.

Referring back to FIG. 19, the measured quantities received by the feedback control device 1902 may be obtained by external measurement devices 1708 such as ultrasound and/or MRI imaging, and optionally by measurements obtained by internal instrumentation 1904 such as heated flow rate sensors or piezoelectric pressure sensors as described previously herein. The feedback control device 1902 processes the measured quantities received from the external measurement devices 1708 and/or internal instrumentation 1904, and transmits a control signal to the adjustment device 1804, which implements the adjustment of the occlusion factor of the vessel flow control device 100. In another aspect, the medical practitioner 1704 may manually input, override, and/or modify the control commands transmitted by the feedback control device 1902.

a. Treatment of Ischemic Stroke

In an aspect, the method described herein above may be used to treat an ischemic stroke in a mammalian patient. In this aspect, the vessel flow control device may be situated within a brain circulatory vessel upstream of an ischemic region. The vessel flow control device may completely occlude the vessel flow while a clot situated downstream of the vessel flow control device is removed. In one aspect, the vessel flow control device may be a dual balloon device implanted such that the clot is situated between the distal balloon and the proximal balloon of the dual balloon device. The dual balloon device may further administer clot-dissolving compounds and/or other treatments to reduce or eliminate the clot from the brain blood vessel. The method described herein above may then be used to gradually restore blood flow, while preventing hemorrhaging of the brain circulatory vessel during the recovery of the patient.

b. Treatment of Tumors

In an aspect, the method described herein above may be used to enhance the effects of chemotherapeutic compounds against tumor cells and/or tissues. In an aspect, the vessel flow control device may be situated within a circulatory vessel responsible for supplying blood to the tumor cells and/or tissue. The vessel flow control device may be configured to reduce the blood flow to the tumor cells and/or tissue, resulting in the shrinkage of the tumor. Upon removal of the tumor, the vessel flow control device may be configured to enhance the blood flow to the tissues surrounding the excised tumor, thereby enhancing the recovery of this surrounding tissue.

c. Treatment of Other Disorders

In an aspect, the method described herein above may be used to enhance the treatment of other disorders including, but not limited to diabetes, aneurisms, stenosis dissolutions, arterial repairs, and any other disorder that may benefit from controlled vessel flow and/or drug release. In an aspect, the occlusion of vessel flow may be coupled with the release of a therapeutic compound in order to lengthen the dwell time of the compound in the vicinity of the target cells and/or tissues. In addition, the vessel flow may be increased after a predetermined treatment time to enhance the removal of the compound from the vessel of the patient.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method for treating a patient having a vessel, the method comprising:
    receiving a delivery device in an internal volume of a variable occlusion element, the internal volume enclosed by an inner member and opening to a proximal opening disposed at a proximal end of a balloon body and a distal opening disposed at a distal end of the balloon body, the delivery device positioning the variable occlusion element in a lumen of the vessel;
    enlarging a toroidal volume as the variable occlusion element inflates, the toroidal volume enclosed by an outer membrane of the balloon body, the outer membrane sealed to the inner member at the proximal end and the distal end; and
    shrinking the toroidal volume as the variable occlusion element deflates, the toroidal volume enlarging or shrinking as the variable occlusion element inflates or deflates between a plurality of occlusion states, each of the plurality of occlusion states including an occlusion factor corresponding to a percentage of a cross-sectional area of the lumen of the vessel occluded by the variable occlusion element.

2. The method of claim 1, wherein the occlusion factor is controlled by a feedback.

3. The method of claim 2, wherein the feedback is at least one of a pressure or a flow of the vessel.

4. The method of claim 1, wherein, the outer membrane has a shape dictated by the occlusion factor.

5. The method of claim 1, wherein the percentage ranges from 5 percent to 100 percent.

6. The method of claim 1, wherein the variable occlusion element selectively transitions between the plurality of occlusion states.

7. The method of claim 1, wherein a subsequent occlusion state of the plurality of occlusion states includes a lower occlusion factor than a current occlusion state when a measurement of vascular leakage indicates no vascular leakage and the subsequent occlusion state includes a higher occlusion factor than the current occlusion state when the measurement of vascular leakage indicates vascular leakage.

8. The method of claim 1, wherein a second balloon body is arranged sequentially with the balloon body, the balloon body and the second balloon body being hydraulically independent of each other.

9. The method of claim 1, wherein the delivery device includes at least one of a guide wire or a catheter.

10. The method of claim 9, wherein the catheter controls vessel flow through the variable occlusion element when the occlusion factor is fully occluded.

11. The method of claim 1, wherein the delivery device controls the toroidal volume by providing pneumatic pressure to inflate or deflate the variable occlusion element.

12. The method of claim 1, wherein the balloon body is made of a semipermeable material, the semipermeable material permitting passive movement of fluid through the variable occlusion element.

13. A method of controlling a blood flow within a lumen of a vessel, the method comprising:
    positioning a variable occlusion element in the lumen by a delivery device, the variable occlusion element made of a semipermeable material configured to allow a passive movement of fluid at least one of into or out of the variable occlusion element;
    deploying the variable occlusion element to an occlusion factor of 100%;
    deflating the variable occlusion element by decreasing the occlusion factor over a time period, the occlusion factor being controlled by a feedback.

14. The method of claim 13, wherein the feedback is a pressure and flow of the vessel.

15. The method of claim 13, wherein the feedback is based on a manual command.

16. The method of claim 13, wherein the feedback is automatic.

17. The method of claim 13, wherein the variable occlusion element includes one or more balloons.

18. The method of claim 13, wherein the variable occlusion element selectively transitions between a plurality of occlusion states.

\* \* \* \* \*